US008278456B2

(12) United States Patent
Robinson et al.

(10) Patent No.: US 8,278,456 B2
(45) Date of Patent: Oct. 2, 2012

(54) SYNTHESIS AND STABILIZATION OF NEUTRAL COMPOUNDS WITH HOMONUCLEAR BONDS

(75) Inventors: Gregory H. Robinson, Athens, GA (US); Yuzhong Wang, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 505 days.

(21) Appl. No.: 12/487,424

(22) Filed: Jun. 18, 2009

(65) Prior Publication Data

US 2010/0041895 A1    Feb. 18, 2010

Related U.S. Application Data

(60) Provisional application No. 61/129,368, filed on Jun. 20, 2008, provisional application No. 61/098,512, filed on Sep. 19, 2008.

(51) Int. Cl.
*C07F 5/02* (2006.01)
*C07F 7/08* (2006.01)
*C07F 9/28* (2006.01)

(52) U.S. Cl. .......... 548/110; 556/413; 562/811; 564/15; 564/8; 568/1; 568/8; 548/111

(58) Field of Classification Search .................. None
See application file for complete search history.

(56) References Cited

U.S. PATENT DOCUMENTS

| | | | |
|---|---|---|---|
| 2,999,735 | A | 9/1961 | Reuschel |
| 4,088,669 | A | 5/1978 | Malek et al. |
| 4,929,322 | A | 5/1990 | Sue et al. |
| 4,946,919 | A | 8/1990 | Johnson |
| 5,034,464 | A | 7/1991 | Arduengo |
| 5,091,498 | A | 2/1992 | Arduengo, III et al. |
| 5,104,993 | A | 4/1992 | Arduengo III |
| 5,196,053 | A | 3/1993 | Dodd et al. |
| 6,660,152 | B2 | 12/2003 | Nayfeh et al. |
| 6,849,244 | B2 | 2/2005 | König et al. |

FOREIGN PATENT DOCUMENTS

WO    WO 98/27064 A1    6/1998

OTHER PUBLICATIONS

Arduengo, A.J., III, "Looking for Stable Carbenes: The Difficulty in Starting Anew," *Acc. Chem. Res.* 32:913-921, American Chemical Society, United States (1999).
Bouhadir, G.; Bourissou, D., "Unusual geometries in main group chemistry," *Chem. Soc. Rev.* 33:210-217, RSC Publishing, England, United Kingdom (2004).
Bourissou, D., et al., "Stable Carbenes," *Chem. Rev.* 100:39-91, American Chemical Society, United States (2000).
Bridgeman, A.J. & Nielsen, N.A., "Multiple bonding in homonuclear Group 13 ethene analogues," *Inorg. Chim. Acta.* 303:107-115, Elsevier B.V., Holland (2000).
Cigler, P., et al., "From nonpeptide toward noncarbon protease inhibitors: Metallacarboranes as specific and potent inhibitors of HIV protease," *PNAS* 102:15394-15399, PNAS, United States (2005).
Colegrove, B.T. & Schaefer, H.F. III, "Disilyne ($Si_2H_2$) Revisited," *J. Phys. Chem.* 94:5593-5602, American Chemical Society, United States (1990).
Corriu, R., et al., "Chemical and photochemical approaches to amino(aryl)silylenes," *J. Organomet. Chem.* 466:55-68, Elsevier Sequoia, Lausanne, Switzerland (1994).
Cowley, A.H., et al., "Structures of and Bonding in Some $A_2X_4$ Molecules," *J. Am. Chem. Soc.* 91:1922-1928, American Chemical Society, United States (1969).
Cowley, A.H., "Some past achievements and future perspectives in main group chemistry," *J. Organomet. Chem.* 689:3866-3872, Elsevier B.V., Holland (2004).
Dagani, R., "Neutral Diborene is a First: Unexpected compound's boron-boron double bond confirmed by calculations," *Chemical & Engineering News* 85:10, American Chemical Society, United States (2007).
De Vries, T. & Vedejs, E., "Electrophilic Activation of Lewis Base Complexes of Borane with Trityl Tetrakis(pentafluorophenyl)borate," *Organometallics* 26:3079-3081, American Chemical Society, United States (2007).
Denk, M., et al., "Synthesis and Structure of a Stable Silylene," *J. Am. Chem. Soc.* 116:2691-2692, American Chemical Society, United States (1994).
Dill, J.D., et al., "Molecular Orbital Theory of the Electronic Structure of Organic Compounds. XXIV. Geometries and Energies of Small Boron Compounds. Comparisons with Carbocations," *J. Am. Chem. Soc.* 97:3402-3409, American Chemical Society, United States (1975).
Dyker, C.A., et al., "Synthesis of an Extremely Bent Acyclic Allene (A "Carbodicarbene"): A Strong Donor Ligand,"*Angew. Chem. Int. Ed.* 47:3206-3209, Wiley-VCH Verlag GmbH & Co. KGaA, Weinheim, Germany (2008).
Giju, K.T., et al., "Stabilization of Tricoordinate Pyramidal Boron: Theoretical Studies on $CBSiH_5$, $BSi_2H_5$, $CBGeH_5$, and $CBSnH_5$," *Angew. Chem., Int. Ed.* 42:539-542, Wiley-VCH Verlag GmbH & Co. KGaA, Weinheim, Germany (2003).
Han, J.S., et al., "Slurry Phase Reaction of Elemental Silicon with Methanol in the Presence of Copper: Direct Synthesis of Trimethoxysilane," *Bull. Korean Chem. Soc.* 30:683-686, Korean Chemical Society, Korea (2009).
Huang, X.-C., et al., "Triple-stranded helices and zigzag chains of copper(I) 2-ethylimidazolate: solvent polarity-induced supramolecular isomerism," *Chem. Commun.* 2232-2234, RSC Publishing, England (2005).
Kaufmann, E. & Schleyer, P.v.R., "Dilithiodiborane(6) ($Li_2B_2H_4$): An Experimentally Viable Species with a B = B Double Bond. Planar No-Bond-Double-Bond Isomers with Pentacoordinate Boron?," *Inorg. Chem.* 27:3987-3992, American Chemical Society, United States (1988).
Keller, P.C., et al., "Reactions of Diborane with Aromatic Heterocytes. 3. Diborane-Catalyzed Polymerization of Imidazole-Borane," *Inorganic Chemistry* 24:2382-2383, American Chemical Society, United States (1985).

(Continued)

*Primary Examiner* — Michael Barker
(74) *Attorney, Agent, or Firm* — Thomas, Kayden, Horstemeyer & Risley, LLP

(57) ABSTRACT

The present invention is directed to the synthesis and stabilization of neutral molecules containing homonuclear single or multiple bonds, methods of preparation, and uses thereof.

13 Claims, 10 Drawing Sheets

OTHER PUBLICATIONS

Kitamura, M., et al., "Unusual Conformational Isomer of 9,10-Dihydro-1,2,3,4,5,6,7,8-octapropylanthracene in Solid State," *Chem. Lett.* 1076-1077, The Chemical Society of Japan, Japan (2002).

Knight, L.B., Jr., et al., "ESR Investigation of the HBBH($X^3\Sigma$) Radical in Neon and Argon Matrices at 4 K. Comparison with *ab Initio* SCF and CI Calculations," *J. Phys. Chem.* 99:16842-16848, American Chemical Society, United States (1995).

Krapp, A., et al., "Orbital Overlap and Chemical Bonding," *Chem. Eur. J.* 12:9196-9216, Wiley-VCH Verlag GmbH & Co. KGaA, Weinheim, Germany (2006).

Kuhn, N., et al., "Derivate des Imidazols, XIII. Carben-Komplexe des Siliciums und Zinns," *Chem. Ber.* 128:245-250, Wiley-VCH Verlagsgesellschaft mbH, Germany (1995).

MacDonald, C.L.B. & Ellis, B.D., in *Encyclopedia of Inorganic Chemistry*, pp. 2718-2730, vol. V, R. B. King, 2nd. Ed., John Wiley & Sons, Inc., United States (2005).

Maier, C.-J., et al., "Blue Tetrakis(diisopropylamino)-*cyclo*-tetraborane and Yellow Tetrakis(tetramethylpiperidino)tetraborata-tetrahedrane," *Angew. Chem., Int. Ed.* 38:1666-1668, Wiley-VCH Verlag GmbH, Weinheim, Germany (1999).

Malatesta, V. & Ingold, K.U., "Kinetic Applications of Electron Paramagnetic Resonance Spectroscopy. 36. Stereoeletronic Effects in Hydrogen Atom Abstraction from Ethers," *J. Am. Chem. Soc.* 103:609-614, American Chemical Society, United States (1981).

Moezzi, A. et al., "Reduction of a Boron-Nitrogen 1,3-Butadiene Analogue: Evidence for a Strong B-B $\pi$-Bond," *Angew. Chem. Int. Ed. Engl.* 31:1082-1083, VCH Verlagsgesellschaft mbH, Germany (1992).

Moezzi, A., et al., "Boron-Boron Double Bonding in the Species $[B_2R_4]^{2-}$: Synthesis and Structure of $[\{(Et_2O)Li\}_2\{Mes_2BB(Mes)Ph\}]$, a Diborane(4) Dianion Analogue of a Substituted Ethylene," *J. Am. Chem. Soc.* 114:2715-2717, American Chemical Society, United States (1992).

Molev, G., et al., "Synthesis, Molecular Structure, and Reactivity of the Isolable Silylenoid with a Tricoordinate Silicon," *J. Am. Chem. Soc.* 128:2784-2785, American Chemical Society, United States (2006).

Nesper, R., et al., in *Organosilicon Chemistry II*: From Molecules to Materials, "Silicon Frameworks and Electronic Structures of Novel Solid Silicides", p. 469-491, N. Auner, J. Weis, Eds. VCH Verlagsgesellschaft mbH, Weinheim, Germany (1996).

Nimlos, M. R., et al., "The electronic states of $Si_2$ and $Si_2^-$ as revealed by photoelectron spectroscopy," *J. Chem. Phys.* 87:5116-5124, American Institute of Physics, United States (1987).

Nöth, H., et al., "Contribution to the Chemistry of Boron, 245. A Boron-Boron Double Bond in the Dianions of Tetra(amino)diborates," *Eur. J. Inorg. Chem.* 1999(11): 1931-1937, Wiley-VCH Verlag GmbH, Germany (1999).

Ottosson, H. & Steel, P.G., "Silylenes, Silenes, and Disilenes: Novel Silicon-Based Reagents for Organic Synthesis?," *Chem. Eur. J.* 12:1576-1585, Wiley-VCH Verlag GmbH & Co. nGaA, Germany (2006).

Pak, C., et al., "Electron Affinities of Silicon Hydrides: $SiH_n$ (n = 0-4) and $Si_2H_n$ (n = 0-6)," *J. Phys. Chem. A* 104:11232-11242, American Chemical Society, United States (2000).

Plesek, J. "Potential Applications of the Boron Cluster Compounds," *Chem. Rev.*, 92:269-278, American Chemical Society, United States (1992).

Power, P.P., "$\pi$-Bonding and the Lone Pair Effect in Multiple Bonds between Heavier Main Group Elements," *Chem. Rev.* 99:3463-3503, American Chemical Society, United States (1999).

Power, P.P., "Homonuclear multiple bonding in heavier main group elements," *J. Chem. Soc., Dalton Trans.* 2939-2951, RSC Publishing, England (1998).

Qin, X.-F., et al.., "Structure and stability of *closo*-$B_nH_{n-2}(CO)_2$ (n = 5-12)," *J. Mol. Struct: Theochem* 810:135-141, Elsevier, Amsterdam (2007).

Qin, X.-F., et al., "Structures and aromaticity of Cationic *closo*-$B_nH_{n-2}(CO)_3^-$(n = 5-12)," *J. Mol. Model.* 13:927-935, Springer-Verlag, Germany (2007).

Ritter, S., "Diatomic Silicon, Main Group Chemistry: Carbene-stabilized Si(o)compound could spark new wave of silicon chemistry," *News of the Week*, WWW.CEN-ONLINE.ORG (2008).

Scott, N. M. & Nolan, S.P., "Stabilization of Organometallic Species Achieved by the Use of N-Heterocyclic Carbene (NHC) Ligands," *Eur. J. Inorg. Chem.*1815-1828, Wiley-VCH Verlag GmbH & Co. KGaA, Weinheim, Germany (2005).

Sekiguchi, A., et al., "A Stable Compound Containing a Silicon-Silicon Triple Bond," *Science* 305 :1755-1757, American Association for the Advancement of Science, United States (2004).

Smith, J.G. & Ho, I., "Reductive Dehalogenations by Alkali Metals and Sodium Naphthalenide. Capture of Solvent-Derived Intermediates," *J. Org. Chem.* 37:4260-4264, American Chemical Society, United States (1972).

So, C.-W., et al., "Synthesis and Characterization of $[PhC(N_tBu)_2]SiCl$: A Stable Monomeric Chlorosilylene," *Angew Chem. Int. Ed.* 45:3948-3950, Wiley-VCH Verlag GmbH & Co. KGaA, Weinheim, Germany (2006).

Steed, J.W., *Frontiers in Crystal Engineering*, 1st ed."Interplay of Non-covalent Bonds: Effect of Crystal Structure on Molecular Structure," pp. 67-90; Tiekink, E. R. T., Vittal, J.J., Eds.: John Wiley & Sons, Ltd.: Chichester, United Kingdom (2006).

Takahashi, M. & Kawazoe, Y., "Theoretical Study on Planar Anionic Polysilicon Chains and Cyclic $Si_6$ Anions with $D_{6h}$ Symmetry," *Organometallics*. 24:2433-2440, American Chemical Society, United States (2005).

Takeda, N., et al., "Reaction of a Sterically Hindered Silylene with Isocyanides: The First Stable Silylene-Lewis Base Complexes," *J. Am. Chem. Soc.* 119:1456-1457, American Chemical Society, United States (1997).

Van Zee, R.J., et al., "$Si_2$, $SiH_3$, and HSiO molecules: ESR at 4 K," *J. Chem. Phys.* 83:6181-6187, American Institute of Physics, United States (1985).

Wang Y. et al., "Planar, Twisted, and Trans-Bent: Conformational Flexibility of Neutral Diborenes," *J. Am. Chem. Soc.* 130:3298-3299, American Chemical Society, United States (2008).

Wang Y. et al., "A Stable Neutral Diborene Containing a B=B Double Bond," *J. Am. Chem. Soc.* 129:12412-12413, American Chemical Society, United States (2007).

Wang, Y., et al., "Carbene-Stabilized Diphosphorous," *J. Am. Chem . Soc.* 130: 14970-14971, American Chemical Society, United States (2008).

Wang, Y., et al., "A Stable Silicon(0) Compound with a Si=Si Double Bond," *Science* 321:1069-1071, (2008), American Association for the Advancement of Science, United States (2008).

Wang, Z.-X., et al., "Isolobal Boron Carbonyl Carbocation Analogs," *J. Theor. Comput. Chem.* 4:669-688, World Scientific Publishing Co., United States (2005).

Weidenbruch, M, "Recent advances in the chemistry of silicon-silicon multiple bonds," *The Chemistry of Organic Silicon Compounds*, 3:391-428, John Wiley & Sons, Ltd., United States (2001).

Weidenbruch, M, "A Stable Silylenoid and a Donor-Stabilized Chlorosilylene: Low-Coordinate Silicon Compounds—A Never-Ending Story?," *Angew. Chem. Int. Ed.* 45:4241-4242, Wiley-VCH Verlag GmbH & Co.-KGaA, Weinheim, Germany (2006).

West, R., et al., "Tetramesityldisilene, a Stable Compound Containing a Silicon-Silicon Double Bond," *Science.* 214:1343-1344, American Association for the Advancement of Science, United States (1981).

Wrackmeyer, B.; et al., "Reactivity of 1,6-Bis(trimethylsilyl)-hexa-3-ene-1,5-diynes towards Triethylborane, Triallylborane, and 1-Boraadamantane: First Molecular Structure of a 4-Methylene-3-borahomoadamantane Derivative, and the First 6,8-Diborabicyclo[2.2.2]oct-2-ene Derivative," *Chem. Eur. J.* 8:1537-1543, Wiley-VCH Verlag GmbH & Co.—KGaA, Weinheim, Germany (2002).

Wu, H.-S., et al., "Monocyclic Boron Carbonyls: Novel Aromatic Compounds," *J. Am. Chem. Soc.* 125:4428-4429, American Chemical Society, United States (2003).

Wu, H.-S., et al., "Structures and Energies of Isolobal $(BCO)_n$ and $(CH)_n$ Cages," *J. Am. Chem. Soc.*, 127:2334-2338, American Chemical Society, United States (2005).

Xie, Y., et al., "The Nature of the Gallium-Gallium Triple Bond," *J. Am. Chem. Soc.* 120:3773-3780, American Chemical Society, United States (1998).

Zhou, M., et al., "Reactions of silicon atoms and small clusters with CO: Experimental and theoretical characterization of SinCO (n = 1-5), $Si_2(CO)_2$, $c$-$Si_2(\mu$-$O)(\mu$-$CSi)$, and $c$-$Si_2(\mu$-$O)(\mu$-$CCO)$ in solid argon," *J. Chem. Phys.* 121:10474-10482, American Institute of Physics, United States (2004).

Zhou, M., et al., "OCBBCO: A Neutral Molecule with Some Boron-Boron Triple Bond Character.," *J. Am. Chem. Soc.* 124:12936-12937, American Chemical Society, United States (2002).

SYNTHESIS AND STABILIZATION OF NEUTRAL COMPOUNDS WITH HOMONUCLEAR BONDS

CROSS REFERENCE TO RELATED APPLICATIONS

This application claims the benefits of U.S. provisional applications 61/129,368, filed Jun. 20, 2008, and 61/098,512, filed Sep. 19, 2008, both of which are incorporated herein by reference in their entirety.

STATEMENT REGARDING FEDERALLY-SPONSORED RESEARCH

Part of the work performed during development of this invention utilized U.S. Government funds under CHI0608142, CHE-0608142, and CHE-0716718 awarded by National Science Foundation. Therefore, the U.S. Government has certain rights in this invention.

BACKGROUND OF THE INVENTION

1. Field of the Invention

The present invention is directed to the synthesis and stabilization of neutral molecules containing homonuclear single or multiple bonds, methods of preparation, and uses thereof.

2. Background Art

Molecules containing C—C multiple bonds are ubiquitous and have been studied for more than two centuries. In contrast, realization of the potential of homonuclear multiple bond chemistry of carbon's immediate neighbors boron and silicon has long frustrated chemists. For instance, it was not until 1981 that a disilene, a compound containing a Si—Si double bond ($R_2Si=SiR_2$, where R is $Me_3C_6H_2$), was prepared by West et al, wherein the central Si atoms were in the formal oxidation states of two (+2). The first disilyne (RSi≡SiR, where R is an extremely bulky ligand), a compound containing a Si—Si triple bond (albeit with a decidedly nonlinear, transbent geometry), was ultimately achieved by Sekiguchi et al. in 2004. The formal oxidation state of Si atoms in Sekiguchi's disilynes was reported to be (+1).

It is well known for transition metals to assume the formal oxidation state of zero in organometallic compounds (for example, $Ni(CO)_4$, $(C_6H_6)_2Cr$, etc.). However, the formal oxidation state of zero is rare for main group elements in their compounds (apart from those in Zintl phases). Si(0) intermediates are promising candidates for the development of new synthetic strategies in silicon chemistry. However, due to their high reactivity and instability, evaluation of Si(0) compounds requires sophisticated instruments and elaborate techniques, such as matrix isolation. The diatomic $Si_2$ molecule, having a triplet ground state ($X^3\Sigma_g^-$), has been studied only in the gas phase and in argon matrices. For instance, the CO complex of the $Si_2$ molecule, $OC:Si=Si:CO$, was examined with argon matrix isolation absorption infrared spectroscopy and computed to have an unusual transbent structure with Si—Si—C angles approaching 90°. However, stabilization of the fleeting diatomic $Si_2$ molecule has never been achieved.

Similarly, no one previously has been able to produce a stable neutral molecule containing a B=B bond. The diboron dianions $[R_2BBR_2]^{2-}$ (I), and their alkali metal salts, were proposed as promising B=B double bond candidates two decades ago. However, corroborating synthetic and structural evidence has been rare. Similarly, the highly reactive parent neutral diborene, HB=BH (II), has only been characterized in matrices.

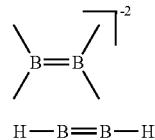

The electron deficiency of boron in (II) lead to theoretical work on its complexation with appropriate Lewis base ligands as a promising approach to viable L(H)B=B(H)L derivatives. Computational prediction of the carbonyl-stabilized diborene, OC(H)B=B(H)CO, was made based on the theoretical development of BCO chemistry. However, such complexes have not been experimentally realized.

The allotropy of phosphorus—white, red, and black—is well documented. Normally, phosphorus prefers a tetrahedral form $P_4$ because P—P pi-bonds are high in energy. Pyrolysis of white phosphorus, $P_4$, yields the high temperature diphosphorus allotrope, gaseous $P_2$. Diphosphorus is very reactive with a bond dissociation energy half that of its ubiquitous lighter congener dinitrogen. The highly reactive and association-prone nature of $P_2$ compared to the legendary inert nature of $N_2$ also raises a question of a possibility to stabilize the $P_2$ molecule.

Generally, diphosphorus functions as four-, six-, and eight-electron donor ligands in transition metal carbonyl complexes. For instance, Cummins and co-workers reported the "mild thermal extrusion" of $P_2$ from niobium diphosphaazide complexes and that the Pt(0) species, $(C_2H_4)Pt(PPh_3)_2$, can serve as a trap for $W(CO)_5$-complexed $P_2$ molecules. In all these examples, $P_2$ behaves as a typical Lewis base by donating its electron pair to the ligand. To our knowledge, no one has been able to synthesize, isolate, and characterize a stable molecule with a $P_2$ nucleus, wherein phosphorous serves as an electron pair acceptor and, thus, mimics the behavior of a Lewis acid.

We now demonstrate stabilization of highly unstable homonuclear species $Si_2$, $B_2H_2$, and $P_2$ with persistent carbene ligands.

BRIEF SUMMARY OF THE INVENTION

The present invention provides stabilized molecules with homonuclear single or multiple bonds, methods for preparing the same, and methods of use thereof.

In one aspect, the present invention provides stable neutral compounds comprising homonuclear bonds. In one embodiment, the compound of the present invention has a formula:

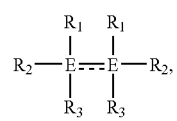

wherein $R_1$ is a Lewis base, $R_2$ and $R_3$ are, independently of each other, absent or are selected from the group consisting of H, F, Br, Cl, I, and combinations thereof, and E is B, Si, or P.

Another aspect of the present invention provides a method of making stable neutral compounds comprising a homonuclear bond. In some embodiments, the method comprises reacting a compound represented by a formula:

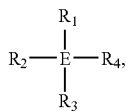

wherein R$_1$ is a Lewis base, R$_2$, R$_3$ and R$_4$ are, independently of each other, absent or are selected from the group consisting of H, F, Br, Cl, I, and combinations thereof, and E is B, Si, or P, with a strong reducing agent.

In another aspect, the present invention provides methods of use of the compounds described herein. In some embodiments, the compounds represented by the formula R$_1$(H)B=B(H)R$_1$ can be used for preparing polymeric materials. In other embodiments, the compounds represented by the formula R$_1$(H)B=B(H)R$_1$ are used for preparation of ceramics. In some embodiments, the compounds of the formula R$_1$Si=SiR$_1$ can be used as delivery vehicles for hyper-pure silicon to surfaces. In one embodiment, the compounds of the formula R$_1$Si=SiR$_1$, wherein R$_1$ is a Lewis base, can be used for preparation of semiconductor devices (e.g., integrated circuits). In yet another embodiment, the compounds represented by the formula R$_1$P=PR$_1$ can be used for preparation of explosives, as a dopant in N-type semiconductors, and for preparation of phosphor bronze.

BRIEF DESCRIPTION OF THE DRAWINGS

FIG. 3. Schematic representation of the HOMO and HOMO-1 orbitals of 3a.

DETAILED DESCRIPTION OF THE INVENTION

Figure 1:
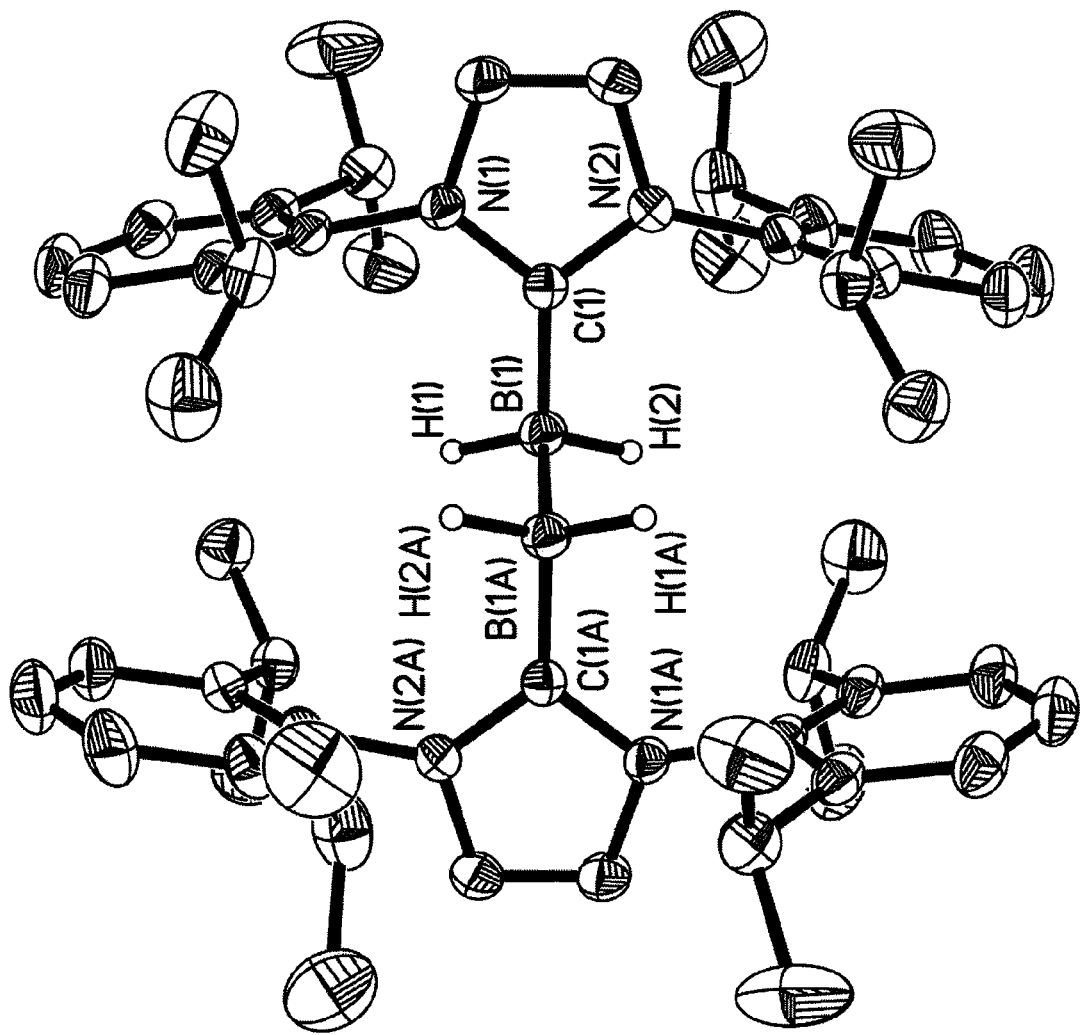
FIG. 1. Molecular Structure of 2 (thermal ellipsoids represent 30% probability: hydrogen atoms on the carbon omitted for clarity). Selected bond distances (Å) and angles (deg): B(1)-B(1A) 1.828(4), B(1)-C(1) 1.577(2), B(1)-H(1) 1.155(18), B(1)-H(2) 1.147(19); B(1A)-B(1)-C(1) 107.45(16), B(1A)-B(1)-H(1) 110.7(9), B(1A)-B(1)-H(2) 110.3(9), C(1)-B(1)-H(1) 108.9(9), C(1)-B(1)-H(2) 108.1(10), H(1)-B(1)-H(2) 111.3(13).

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention.

The embodiment(s) described, and references in the specification to "one embodiment", "an embodiment", "an example embodiment", etc., indicate that the embodiment(s) described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

As used herein, the term "Lewis acid" refers to a chemical compound that can accept a pair of electrons. "Lewis base", as used herein, refers to a chemical compound capable of donating a pair of electrons. The term "homonuclear bond" refers to a covalent bond formed between two of the same elements. As used herein, the term "reducing agent" refers to a chemical element or a chemical compound that donates electrons in a process of a chemical reaction, thereby reducing another species and being oxidized in the process.

As used herein, the acronym "HOMO" is meant to refer to the highest occupied molecular orbital, the acronym "NBO" refers to the natural bond orbital, and the acronym "LMO" refers to localized molecular orbital.

I. Stable Neutral Molecules with Homonuclear Bonds

Previously, molecules containing homonuclear bonds of the present invention were only present either in theoretical models, or in highly reactive and unstable gas phases, and were examined only by entrapment in argon matrices. An aspect of the present invention provides a stable neutral compound comprising a homonuclear double bond. The term, "stable" refers to a molecule that does not decompose at ambient temperature under the protection of argon. The term "neutral molecule" refers to a molecule that can exist on its own, in a neutral state, so that when it binds to another moiety, it does not contribute to the overall charge of the new molecule.

In some embodiment, the compound of the present invention is represented by the formula:

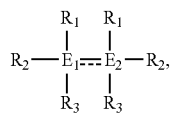

wherein
$R_1$ is a Lewis base, $R_2$ and $R_3$ are, independently of each other, absent or are selected from the group consisting of H, F, Br, Cl, I, and combinations thereof, and $E_1=E_2$ and is B, Si, or P; with the proviso that when E is B, and ----is ==, $R_2$ is absent and $R_3$ is H, F, Br, or Cl;

when E is B and ----is ----, $R_2$ and $R_3$ are, independently of each other, H, F, Br, or Cl;

when E is Si, and ----is ==, both $R_2$ and $R_3$ are absent;

when E is Si, and ----is ----, $R_2$ is absent and $R_3$ is H, F, Br, Cl, or I;

when E is P and ----is ----, both $R_2$ and $R_3$ are absent.

In some embodiments, Lewis base suitable for use in the present invention is a persistent carbene. The term "persistent carbene" means a stable carbene demonstrating certain stability despite being a reactive intermediate. The term "NHC" stand for N-heterocyclic carbene, and is a type of a persistent carbene. In some embodiments, a persistent carbene comprises imidazole-2-ylidenes, triazole-5-ylidenes, cyclic diaminocarbenes, acyclic diaminocarbenes, heteroaminocarbenes, and combinations thereof. Examples of suitable carbenes include, but are not limited to, :C{N(SiR$^x_3$)CH}$_2$, wherein R$^x$ is methyl, tert-butyl, monoalkylaryl, dialkylaryl, trialkylaryl, dialkylamido, :C{N(2,6-Pr$^j_2$C$_6$R$^y_3$)CH}$_2$, :C(NHCH)$_2$, :C{N(Pr$^j$)C(CR$^y_3$)}$_2$, :C{N(2,4,6-Me$_3$C$_6$R$^y_2$)CH}$_2$, wherein R$^y$ is, independently, H, F, Br, Cl, or I.

One embodiment of the invention presents a compound of the formula:

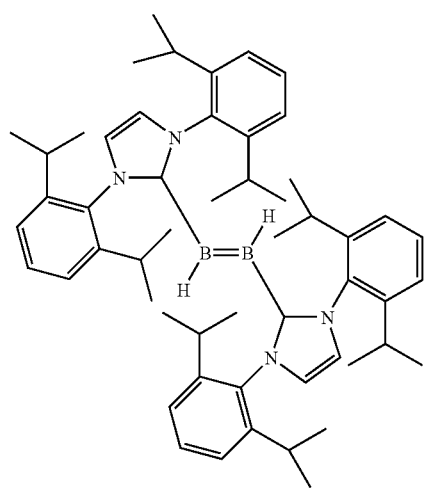

In another embodiment, the compound of the present invention is represented by the formula:

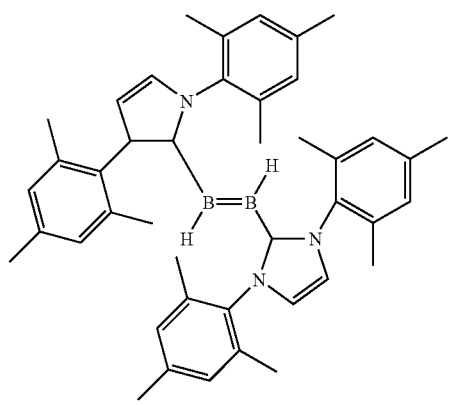

In yet another embodiment, the compound of the present inventions is:

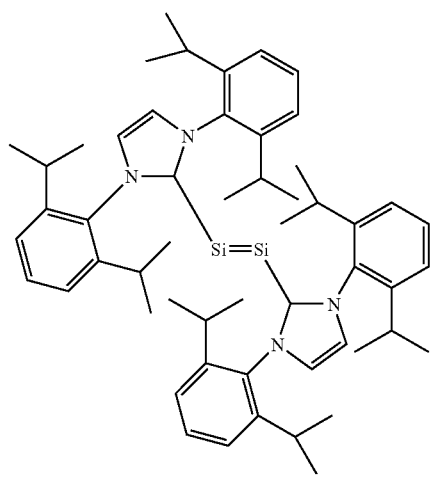

In certain embodiments, the compound of the present invention is:

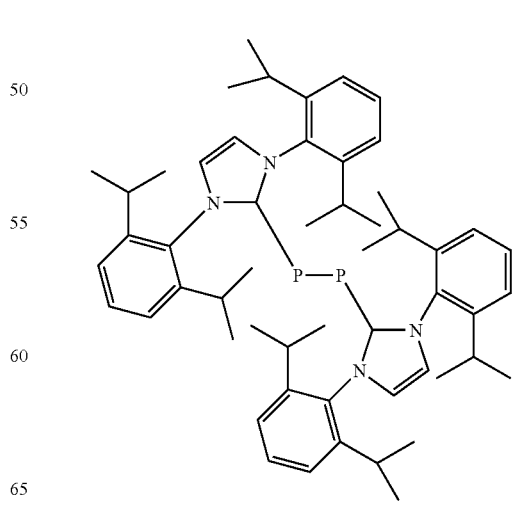

In certain other embodiments, the compound of the present invention is:

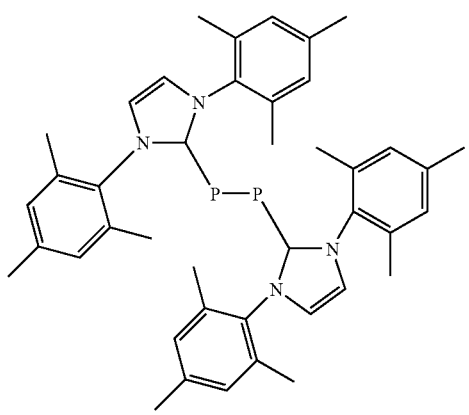

In one embodiment, the compound of the present inventions is represented by the formula:

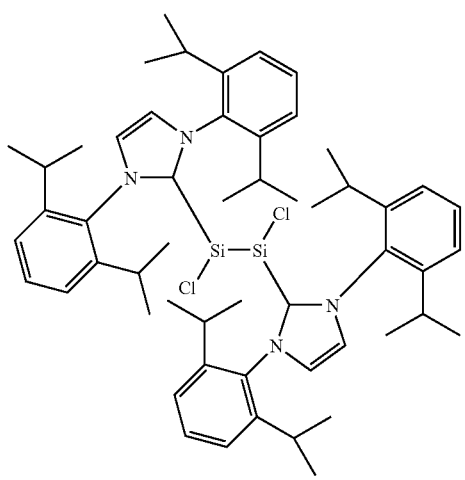

In yet other embodiments, the compound of the present invention is:

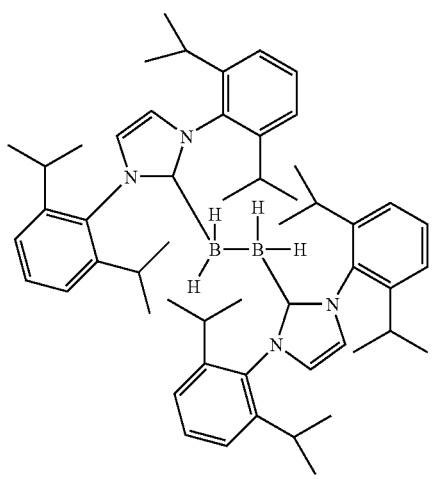

In another embodiment, the compound is:

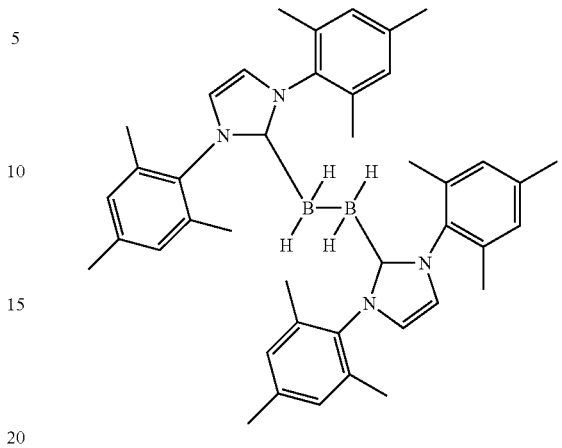

II. Method of Making Stable Neutral Molecules with Homonuclear Bonds

One aspect of the present invention presents a method of making stable neutral molecules with homonuclear bonds. It is understood that the description herein is but one embodiment for making stabilized neutral molecules with homonuclear bonds. In some embodiments, the method comprises reacting a starting material with a strong reducing agent. In some embodiments, a suitable starting material is represented by the formula:

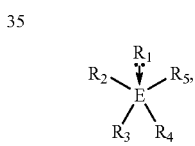

wherein $R_1$ is a Lewis base, $R_2$, $R_3$ $R_3$ and $R_5$ are, independently of each other, absent or are selected from the group consisting of H, F, Br, Cl, I, and combinations thereof, and E is B, Si, or P.

In some embodiments of the present invention, the suitable starting material is a compound:

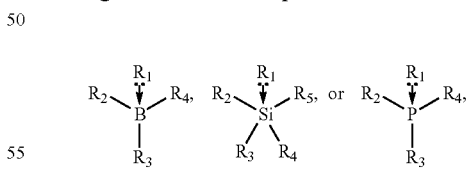

wherein $R_1$ is a carbene selected from the group consisting of imidazole-2-ylidenes, triazole-5-ylidenes, cyclic diaminocarbenes, acyclic diaminocarbenes, heteroaminocarbenes, and combinations thereof, $R_2$, $R_3$, $R_4$, and $R_5$ are selected from the group consisting of H, F, Br, Cl, and I.

In this embodiment, starting materials are prepared by any suitable techniques known to those skilled in the art and guided by the teachings herein provided. Compounds

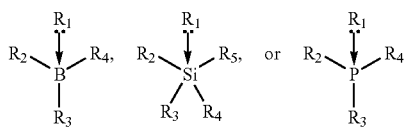

can be prepared, for example, by reacting compounds

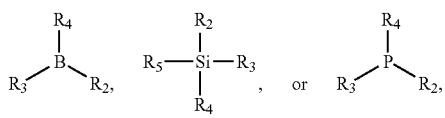

wherein $R_2$, $R_3$, $R_4$, and $R_5$ are selected from the group consisting of H, F, Br, Cl, and I, with a carbene selected from the group consisting of :C$\{$N(SiR$^x_3$)CH$\}_2$, wherein R$^x$ is methyl, tert-butyl, monoalkylaryl, dialkylaryl, trialkylaryl, dialkylamido, :C$\{$N(2,6-Pr$^i_2$C$_6$R$^y_3$)CH$\}_2$, :C(NHCH)$_2$, :C$\{$N(Pr$^i$)C(CR$^y_3$)$\}_2$, :C$\{$N(2,4,6-Me$_3$C$_6$R$^y_2$)CH$\}_2$, wherein R$^y$ is, independently, H, F, Br, Cl, or I, and combinations thereof, in a suitable solvent. Examples of a solvent suitable for the present invention include, but are not limited to, hexane, benzene, toluene, diethyl ether, tetrahydrofuran (THF), or combinations thereof. In one embodiment, $R_1$SiCl$_4$, wherein $R_1$ is :C$\{$N(2,6-Pr$^i_2$C$_6$H$_3$)CH$\}_2$, is prepared by reacting SiCl$_4$ with :C$\{$N(2,6-Pr$^i_2$C$_6$H$_3$)CH$\}_2$ in hexane at room temperature for several hours. In another embodiment, $R_1$BBr$_3$, wherein $R_1$ is :C$\{$N(2,6-Pr$^i_2$C$_6$H$_3$)CH$\}_2$, is prepared by reacting BBr$_3$ with :C$\{$N(2,6-Pr$^i_2$C$_6$H$_3$)CH$\}_2$ in diethyl ether at room temperature for several hours. In an alternative embodiment, $R_1$BBr$_3$, wherein $R_1$ is :C $\{$N(2,4,6-Me$_3$C$_6$H$_2$)CH$\}_2$, is prepared by reacting BBr$_3$ with :C $\{$N(2,4,6-Me$_3$C$_6$H$_2$)CH$\}_2$ in diethyl ether at room temperature for several hours. In yet other embodiments, $R_1$PCl$_3$, wherein $R_1$ is :C$\{$N(2,4,6-Me$_3$C$_6$H$_2$)CH$\}_2$ or :C$\{$N(2,6-Pr$^i_2$C$_6$H$_3$)CH$\}_2$, is prepared by reacting $R_1$PCl$_3$ with :C$\{$N(2,4,6-Me$_3$C$_6$H$_2$)CH$\}_2$ or :C$\{$N(2,6-Pr$^i_2$C$_6$H$_3$)CH$\}_2$ in THF at room temperature for several hours.

Starting material

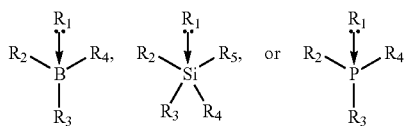

wherein $R_1$ is a carbene selected from the group consisting of imidazole-2-ylidenes, triazole-5-ylidenes, cyclic diaminocarbenes, acyclic diaminocarbenes, heteroaminocarbenes, and combinations thereof, $R_2$, $R_3$, $R_4$, and $R_5$ are selected from the group consisting of H, F, Br, Cl, and I, can be further reacted with a strong reducing agent in a suitable solvent under suitable reaction conditions. A skilled artisan will be familiar with a plethora of reducing agents and solvents available for the purposes of the present invention. Examples of a suitable reducing agent include, but are not limited to, KC$_8$, LiAlH$_4$, NaBH$_4$, DIBAL, Na(Hg), K(Hg), LiH, alkali and alkali earth metals and their alloys, and nascent hydrogen. Examples of a suitable solvent include, but are not limited to, ethers and their mixtures, such as dimethyl ether, diethyl ether, THF, dioxane, dimethoxyethane, methoxybenzene, and ethylene oxide. A skilled artisan will understand that the reaction temperature and time can be varied in order to optimize the yield of the desired product. In some embodiments, the reduction of the starting material will be conducted at a temperature range from about 20° C. to about 30° C. In other embodiments, the reduction of the starting material will be carried out at about 25° C. The time of the reaction can be varied from about one hour to about eight hours. In some embodiments, the reduction will be allowed to proceed for six hours. In one embodiment, the reaction conditions can be chosen, for example, to be reacting any of the compounds $R_1$BBr$_3$, $R_1$SiCl$_4$, or $R_1$PCl$_3$, wherein $R_1$ is :C$\{$N(2,6-Pr$^i_2$C$_6$H$_3$)CH$\}_2$ or :C$\{$N(2,4,6-Me$_3$C$_6$H$_2$)CH$\}_2$, with KC$_8$ at 25° C. for six hours.

The ratio between the starting material and the reducing agent can be varied in order to achieve the highest yield of the compound of the present invention. In some embodiments, the ratio between the starting material and the reducing agent is from about 1 to about 10. In other embodiments, the ratio between the starting material and the reducing agent is from about 1 to about 6. In certain other embodiments, the ratio between the starting material and the reducing agent is from about 1 to about 5. In yet other embodiments, the ratio between the starting material and the reducing agent is from about 1 to about 4 or from about 1 to about 3. In one embodiment, the ratio between $R_1$SiCl$_4$, wherein $R_1$ is :C$\{$N(2,6-Pr$^i_2$C$_6$H$_3$)CH$\}_2$, and KC$_8$ is 1:4. In another embodiment, the ratio between $R_1$BBr$_3$, wherein $R_1$ is :C$\{$N(2,6-Pr$^i_2$C$_6$H$_3$)CH$\}_2$, and KC$_8$ is 1:5.4. In an alternative embodiment, the ratio between $R_1$BBr$_4$, wherein $R_1$ is :C $\{$N(2,4,6-Me$_3$C$_6$H$_2$)CH$\}_2$, and KC$_8$ is 1:5. In yet other embodiments, the ratio between $R_1$PCl$_3$, wherein $R_1$ is :C$\{$N(2,6-Pr$^i_2$C$_6$H$_3$)CH$\}_2$ or :C$\{$N(2,4,6-Me$_3$C$_6$H$_2$)CH$\}_2$, and KC$_8$ is 1:3.1.

The compound of the present invention can be isolated from the reaction mixture by the standard procedures known to a person of ordinary skill in the art and guided by the teachings herein. For example, the compound of the present invention can be recrystallized directly from the parent solvent. Alternatively, the compound can be extracted by a suitable solvent, and then recrystallized from the extraction solvent. A single-solvent recrystallization can be performed in order to isolate the compound of the present invention. Alternatively, a multi-solvent recrystallization is preformed. Examples of solvents suitable for the present invention include, but are not limited to, solvents and their mixtures, such as diethyl ether, THF, hexane, benzene, and toluene.

III. Method of Use of Stable Neutral Molecules with Homonuclear Bonds

In another aspect, the present invention provides methods of use of the compounds described herein. In some embodiment, the compounds of the formula $R_1$Si=SiR$_1$, wherein $R_1$ is as defined herein, can be used in any application that requires utilization of elemental silicon. Examples of elemental Si use include, but are not limited to, semiconductor devices, integrated circuits, microchips, photovoltaic (solar) cells, and rectifiers; as raw material in the manufacture of organosilicic and silicon resins, seals and oils; manufacture of alloys such as iron, steel, aluminum, and copper alloys; and nanotechnology.

The use of silicon in photovoltaic area and semiconductor technology demands very high purity Si. Although a number of methods are available for production of hyper-pure elemental silicon, most of them suffer from production of impurities. Additionally, some methods of silicon production are not eco-friendly, as they result in emission of large quantities of carbon dioxide. In some embodiments, compounds of the present invention of the formula $R_1$Si=SiR$_1$, wherein $R_1$ is as defined herein, can be used for environmentally-friendly production of hyper-pure elemental silicon. In one embodiment, hyper-pure elemental Si can be produced by exposing the compounds of the present invention to low temperatures under high vacuum. These conditions should afford decomposition of the compound of the present invention and sublimation of carbene ligands, producing hyper-pure elemental Si. In some embodiments, pure elemental silicon can be produced by including a silicon seed (e.g. small silicon particles) in the process of production. As described herein, the compound of the present invention, when exposed to the conditions suitable for its decomposition, should yield hyper-pure elemental Si, which can be collected on the surface of the small silicon particles provided, thus enlarging them. Resulting macroparticles of pure elemental silicon can be easily collected, transported, and utilized as needed. In another embodiment, the compound of the present invention can be used for plating a thin layer of elemental silicon onto various surfaces. By a way of an example, a thin film of the compound of the present invention can be plated onto a suitable surface (e.g., metal) by exposing the compound of the present invention to ionizing radiation. This should result in generation of ions of elemental silicon, which can be deposited onto a provided substrate, resulting in a surfaces plated with a layer of silicon of a desired thickness. In other embodiments, individual atoms of hyper-pure silicon can be produced by exposing the compounds of the present invention to high temperatures with or without vacuum. Under these conditions, the compounds of the present invention should decompose into carbene ligands and elemental silicon. The ligands are expected to vaporize, leaving hyper-pure elemental silicon adhered to a provided surface. Alternatively, it is further expected that exposing the compounds of the present invention to electromagnetic radiation would disrupt bonding, producing volatile carbene ligands and elemental silicon. The wavelength of the radiation would be selected depending on the energy required to break a bond between the ligands and silicon atoms. Removal of thus formed gas should leave behind a hyper-pure elemental silicon.

Yet in other embodiments, the compounds of the present invention can be used as precursors for many silicon-containing compounds. Examples of such compounds include, but are not limited to, silicides, silicates, silicones, silanes, and siloxanes. Such compounds could be prepared by, for example, directly contacting the compound of the present invention with various metals (e.g., Ni, Mg, Sr, Pt, Ti) or non-metals (e.g., $O_2$, C, F) after, during, or before exposing it to conditions suitable for decomposition of the present compounds and evaporation of carbene ligands, as described herein. Additionally, the compounds of the present invention could find their use in manufacture of alloys, such as aluminum-silicon alloys for automotive industry. Such alloys could be produced by first exposing the compounds of the present invention to high temperatures with or without vacuum, followed by combining the resulting elemental silicon with aluminum.

In other embodiments, the compounds represented by the formula $R_1(R_3)B=B(R_3)R_1$, wherein $R_1$ and $R_3$ are as defined herein, can be used for preparing polymeric materials. Diborene polymerization could be achieved by subjecting the compounds of the present invention to an electromagnetic radiation in the presence of a suitable catalyst. The wavelength of the radiation would be selected depending on the energy required to break a double bond between boron atoms, yet to keep the integrity of the B—B single bond. This amount of energy should also be sufficient to break a bond between the ligand and the boron atoms. Diborene polymerization can be promoted, for example, by a catalyst (e.g. chromium trioxide, titanium halides, and metallocenes), while carbene ligands would be expected to vaporize. The resulting polymer can be made linear or branched, and would have the formula:

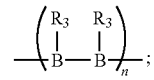

wherein $R_3$ is as defined herein, and n is an integer of a value of at least 1. The physical properties of these polymers can be adjusted based on the extent and type of branching, their density, and the molecular weights. These polymers are expected to be more biodegradable than a typical polyethylene polymer due to the smaller B—B bond energy compared to the C—C bond energy.

In other embodiments, the compounds represented by the formula $R_1(R_3)B=B(R_3)R_1$ are used for preparation of ceramics. In some embodiment, a boron-based ceramic can be prepared by subjecting the compounds of the present invention to heat, followed by cooling. Ceramics prepared from the compounds of the present invention are expected to have unique physical properties, and should find a wide range of applications, for example in gas burner nozzles, ballistic protection, nuclear fuel uranium oxide pellets, bio-medical implants, jet engine turbine blades, and missile nose cones. In other embodiments, compounds of the present invention should find their application in manufacturing of borosilicate glass. Borosilicate glass can be manufactured by adding the compounds of the present invention to the composition comprising silicate sand, soda, and ground lime. Heating of this mixture at temperatures sufficient to promote a reaction between the compound of the present invention and other reactants, as described herein, would be expected to produce borosilicate glass of high resistance to breaking. In yet other embodiments, the compound of the present invention can be used as a dopant in the semiconductor industry. Hyper-pure silicon produced as described herein can be doped by an ultra pure boron by addition of the compounds of the formula $R_1(R_3)B=B(R_3)R_1$ to the reaction mixture.

In yet other embodiments, the compounds represented by the formula $R_1P=PR_1$ can be used for preparation of explosives, as a dopant in N-type semiconductors, and for preparation of organophosphorus compounds with many applications, including in plasticizers, flame retardants, pesticides, extraction agents, and water treatment. Typically production of phosphorus takes place at large facilities and it is transported heated in liquid form. However, due to its explosive nature, major accidents have occurred during transportation of pure phosphorous, leading to large fires. In one embodiment, the compounds of the present invention can be used as a non-explosive precursor to various chemicals (e.g. the herbicide glyphosate). In another embodiment, the compounds represented by the formula $R_1P=PR_1$, can be used for preparation of phosphoric acid for food applications such as soda beverages, as a starting point to make food grade phosphates (e.g., mono-calcium phosphate which is employed in baking powder and sodium tripolyphosphate), and to improve the characteristics of processed meat and cheese. Phosphoric acid can be manufactured by exposing the compounds of the present invention to high temperatures to produce phosphorus pentoxide, followed by dissolution in dilute phosphoric acid. This process should produce a food-grade, very pure thermal phosphoric acid without any arcenic contaminants typically found when elemental phosphorous is extracted from a rock.

EXAMPLES

Example 1

Synthesis and Characterization of R'(H)$_2$B—B(H)$_2$R' and R'(H)B=B(H)R' (R'=:C{N(2,6-Pr$^i_2$C$_6$H$_3$)CH}$_2$)

RBBr$_3$, 1 was reacted with KC$_8$ in diethyl ether and isolated two products: 2, R(H)$_2$B—B(H)$_2$R, as air-stable, colorless block crystals, and compound 3 as air-sensitive, orange/red sheet-like crystals.

Equation 1.

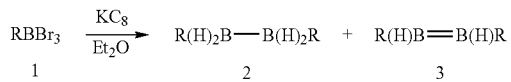

(1)

The stoichiometric ratio of 1 to KC$_8$ has been observed to affect the yield of 3. A higher yield of 3(12%) was obtained with a stoichiometric 1:KC$_8$ ratio of 1:5.4. Greater amounts of KC$_8$ decrease the yield of 3. At a 1:KC$_8$ ratio of 1:9, only 2 was isolated. The unexpected formation of 2 and 3 appears to involve the well documented hydrogen abstraction from ethereal solvents in the presence of alkali metals.

We also prepared the carbene:borane adduct, R:BH$_3$, 4. The $^{11}$B NMR resonances of 4 (RBH$_3$), 2 (R(H)$_2$B—B(H)$_2$R), and 3 (R(H)B=B(H)R) are −35.38, −31.62, and +25.30 ppm, respectively. The $^{11}$B signal of 4 is a quartet ($J_{BH}$=83.38 Hz), while 2 displays a singlet with shoulders ($\omega_{1/2}$) 188 Hz) and 3 displays a broad singlet ($\omega_{1/2}$=946 Hz). The $^1$H NMR imidazole resonances of 4, 2, and 3 are 6.31, 6.21, and 6.14 ppm, respectively.

X-ray structural analysis reveals that 2 has a center of symmetry about the (H)$_2$B—B(H)$_2$ core (FIG. 1). The hydrides (B—H) in 2, 3, and 4 were located in the difference Fourier map. The B—B bond distance in 2(1.828(4) Å) compares well to that computed for the CO-ligated analogue OC(H)$_2$BB(H)$_2$CO (1.819 Å) and to those in an activated m-terphenyl based diborate (1.83(2) Å) as well as a 2,3-diboratabutadiene dianion (1.859(8) Å). However, the bond distance in 2 is longer than those in three-coordinate diboron compounds (1.682(16) to 1.762(11) Å). The boron atoms in 2 reside in tetrahedral geometries. The N$_2$C$_3$ ring of the NHC ligand is almost perpendicular to the B—B—C plane with a N(1)-C(1)-B(1)-B(1A) torsion angle of −89.3°. The B—C bond distance in 2 (1.577(2) Å) is somewhat shorter than that in 1 (1.623(7) Å), but is similar to that in 4 (1.585(4) Å).

Figure 2:
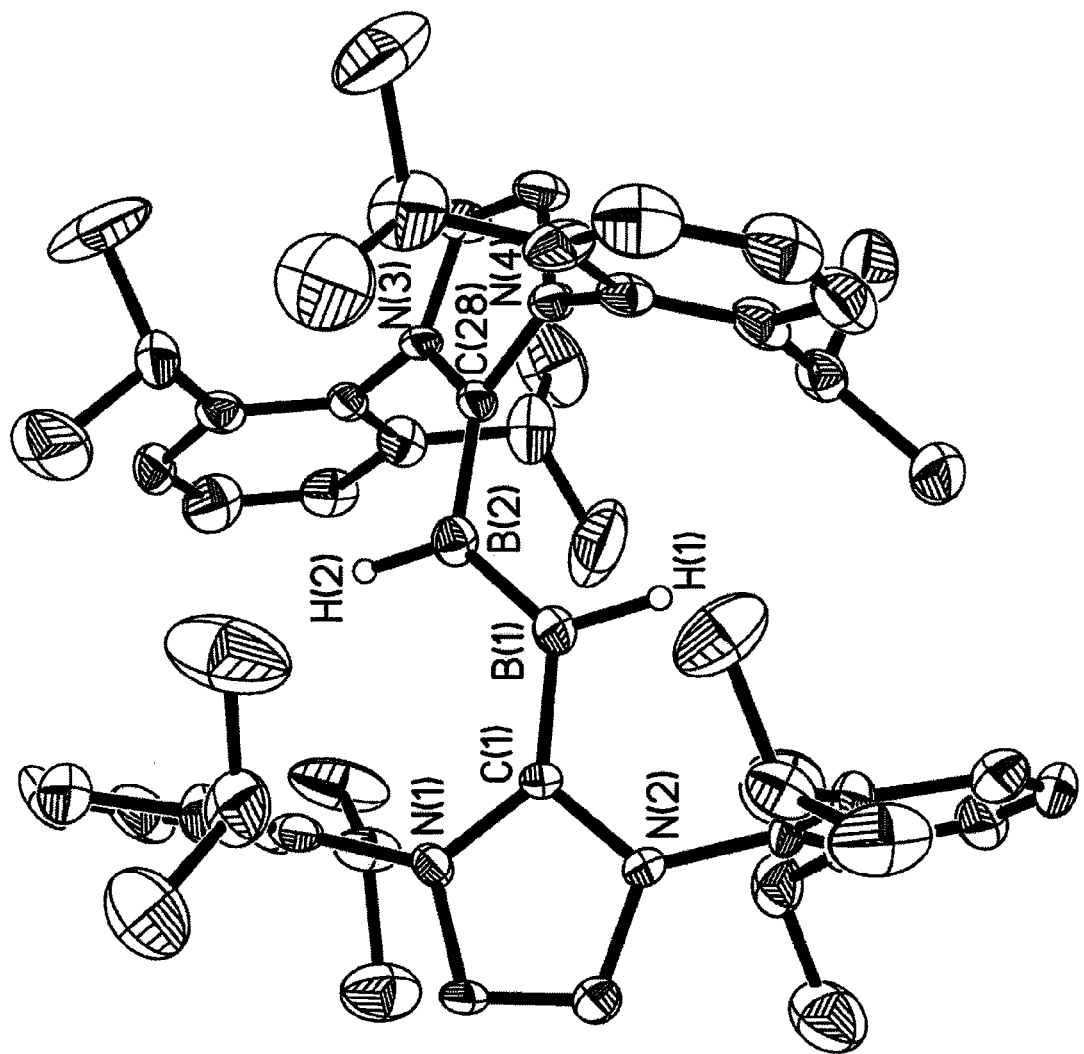
FIG. 2. Molecular structure of 3 (thermal ellipsoids represent 30% probability; hydrogen atoms on carbon omitted for clarity). Selected bond distances (Å) and angles (deg): B(1)-B(2) 1.561(18), B(1)-C(1) 1.543(15), B(1)-H(1) 1.14(2), B(2)-C(28) 1.532(15), B(2)-H(2) 1.13(2); B(2)-B(1)-C(1) 128.3(12), B(2)-B(1)-H(1) 124(4), C(1)-B(1)-H(1) 107(4), B(1)-B(2)-C(28) 126.1(12), B(1)-B(2)-H(2) 128(4), C(28)-B(2)-H(2) 105(4)

Compound 3 crystallizes in the orthorhombic space group P2$_1$2$_1$2$_1$ (No. 19). Each asymmetric unit contains two independent, and nearly identical, molecules of 3 (FIG. 2; only one molecule of 3 is shown). The B—C bond distances, 1.547(15) Å (average), are marginally shorter than those of 1, 2, and 4. Moreover, in contrast to 2, one C$_3$N$_2$ carbene ring of 3 is nearly coplanar with the B$_2$H$_2$ core (N(1)-C(1)-B(1)-B(2) torsion angle, −13.8°), while the other is staggered more (N(4)-C(28)-B(2)-B(1) torsion angle, −30.0°). The three-coordinate boron atoms in 3 adopt trigonal planar geometries. The most notable feature of 3, however, is the B=B bond. The B=B bond distance of 1.560(18) Å (average) in 3 is not only considerably shorter than the B—B distance in 2(1.828 (4) Å), but also shorter than those reported for [Mes$_2$BB (Mess)Ph]$^{2-}$ (1.636.-(11) Å) and for [{Ph(Me$_2$N)BB(NMe$_2$) Ph}]$^{2-}$ (1.627 Å (average)), which purportedly contained a "strong B—B π-bond". Furthermore, the B=B bond distance in 3 compares well to those in dianionic tetra(amino)diborates (1.566(9) to 1.59(1) Å) and to the computed B=B bond lengths for the OC(H)B=B(H)CO ((IV), L:=CO) analogue (1.590 Å) and for diborene, (II) (1.498-1.515 Å). The computed B—B distance of 1.45 Å reported for OCBBCO, a compound "with some triple bond character", is shorter. Notably, the B—B bond distance difference of 0.27 Å between 2 and 3 is comparable to the corresponding difference (about 0.2 Å) between ethane and ethene. Likewise, the C—C bond distance difference of 0.1 Å between ethene and ethyne corresponds to the difference between 3 and OCBBCO (0.11 Å). Thus, the structural details of 3 are consistent with a B=B double bond.

Figure 3:
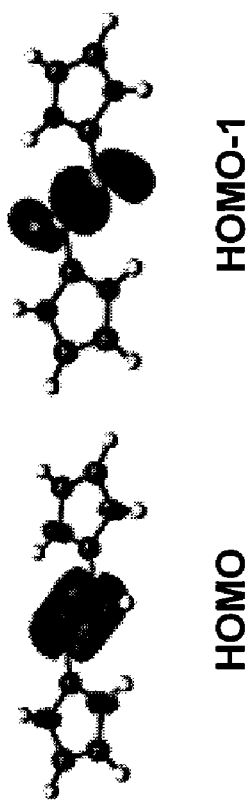

The nature of 3 was investigated by performing B3LYP/6-311+G** DFT computations on the simplified R(H)B=B(H) R(R=:C(NHCH)$_2$) model, 3a (FIG. 3). Both 3a and the OC(H)B=B(H)CO ((III), ligand=CO) analogue are planar and have C$_{2h}$ symmetry, whereas the corresponding R moieties in 3 are twisted because of the greater steric demands of the very bulky N(aryl) ligands. The computed B—B bond lengths in 3a (1.591 Å) and (III) (ligand=CO) (1.590 Å) are virtually identical and are close to the error bound of the corresponding experimental distance of 3(1.561(18) Å). The B—C length (1.547(15) Å (average)) of 3 also agrees with the computed value (1.531 Å) for 3a. Perhaps due to reduced steric repulsion between the ligands, the B—B—C bond angle in 3a (120°) is less than the average value in 3, 126.7 (12)°.

The HOMO of 3a (FIG. 3) is mainly a B—B π-bonding orbital involving the overlap of boron 2p orbitals, while the HOMO-1 has mixed B—B and B—H σ-bonding character. Double check in provisional Natural bond orbital (NBO) electron occupancies of the B—B σ- and π-bonding orbitals in 3a are 1.943 and 1.382, respectively. The Wiberg and NLMO/NPA B—B bond indices, 1.408 and 1.656, respectively, also document the B=B double bond character in 3a.

The computed boron-boron Wiberg bond indexes along the OC(H)$_2$B—B(H)$_2$CO (ethane-like), OC(H)B=B(H)CO ((III), ligand=CO) (ethene-like), and OCBBCO (ethyne-like) series, 0.870, 1.308, and 1.953, respectively, are instructive. The 1.0, 2.0, 3.0 unit bond order values of the hydrocarbon series are not to be expected for the corresponding boron-boron analogues owing to the resonance contributions of Lewis structures. Nevertheless, the single-, double-, and triple-bond descriptions of boron-boron bonds discussed here are appropriate.

Example 2

Synthesis and Characterization of R'(H)$_2$B—B(H)$_2$R' and R'(H)B=B(H)R' (R'=:C{N(2,4,6-Me$_3$C$_6$H$_2$) CH}$_2$)

The reaction of R'BBr$_3$ with KC$_8$ in a 1:5 ratio in Et$_2$O resulted in isolation of red-colored 5(15.8%), together with colorless 6, R'(H)$_2$B—B(H)$_2$R'. Reduction using a R'BBr$_3$:KC$_8$ ratio of 1:6.2 only resulted in 6. Similar to the formation of 2 and 3, the preparation of 5 and 6 involves the well-documented hydrogen abstraction from ethereal solvents in the presence of alkali metals. Both 5a, as black red crystals, and 5b, as ruby-colored crystals, were isolated from the 1:5 Et$_2$O/hexane solvent mixture, while 5c was crystallized from the parent Et$_2$O solution.

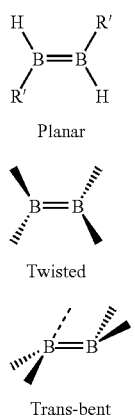

Planar

Twisted

Trans-bent

While trans-bent geometries of the heavier group 13 dianionic alkene analogues, [H$_2$E=EH$_2$]$^{2-}$ (E=Al, Ga, In), are predicted to be favored over planar alternatives, both diboron dianions (E=B) and the Lewis base-stabilized neutral diborenes (3 and OC(H)B=B(H)CO) prefer planar geometries. Hence, the twisted (5b) and trans-bent (5c) structures of 5 are unexpected. The pyramidal tricoordinate boron atoms in 5c contrast with the predominant trigonal planar geometries. Indeed, pyramidal boron environments have only been reported in cyclic systems.

Despite their three different conformations in the solid state, 5a-c, exhibit identical $^1$H and $^{11}$B NMR spectra in C$_6$D$_6$ solution. Furthermore, the broad singlet $^{11}$B NMR resonance of 5 (+23.45, ω$_{1/2}$=587 Hz) corresponds to that of diborene 3 (+25.30, ω$_{1/2}$=946 Hz). The $^1$H NMR imidazole resonances of 5 and 6 are 5.96 and 5.91, respectively. There is no evidence for different isomers or states of 5 in solution. We conclude that 5a-c are polymorphs—the same compound crystallizing in different forms. The space groups for 5a-c are P2$_1$/c, P-1, and P2$_1$/c, respectively, and their packing patterns are completely different.

The $^{11}$B signal of 6(−31.20) is a triplet (J$_{BH}$=83.38 Hz) like that of diborane 2(−31.62). The core of 6 consists of two tetrahedral C(H)$_2$B units connected by a boron-boron single bond (1.795(5) Å).[18] Evidently due to the smaller steric repulsion between the carbene ligands, the B—B distance in 6 is shorter than that in 2(1.828(4) Å).

Figure 4:
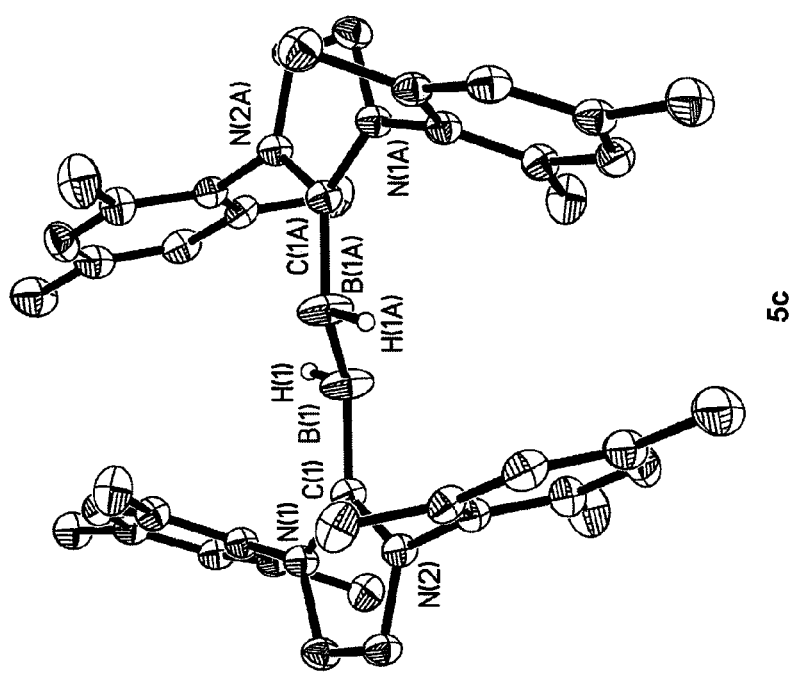
FIG. 4. Molecular structures of 5b and 5c (thermal ellipsoids represent 30% probability; hydrogen atoms on carbon are omitted for clarity). Selected bond distances (Å) and angles (deg): For 5b, B(1)-B(2) 1.582(4), B(1)-C(1) 1.541(4), B(2)-C(22) 1.541(4), B(1)-H(1) 1.117(17), B(2)-H(2) 1.12(3); C(1)-B(1)-B(2) 125.0(2), C(1)-B(1)-H(1) 109.9(16), B(2)-B(1)-H(1) 124.9(16), C(22)-B(2)-B(1) 125.1(2), C(22)-B(2)-H(2) 107.0(15), B(1)-B(2)-H(2) 127.2(15). For 5c, B(1)-B(1A) 1.679(9), B(1)-C(1) 1.565(5), B(1)-H(1) 1.109(18); C(1)-B(1)-B(1A) 118.6(5), C(1)-B(1)-H(1) 107.7(19), H(1)-B(1)-B(1A) 118(2).
Figure 4:
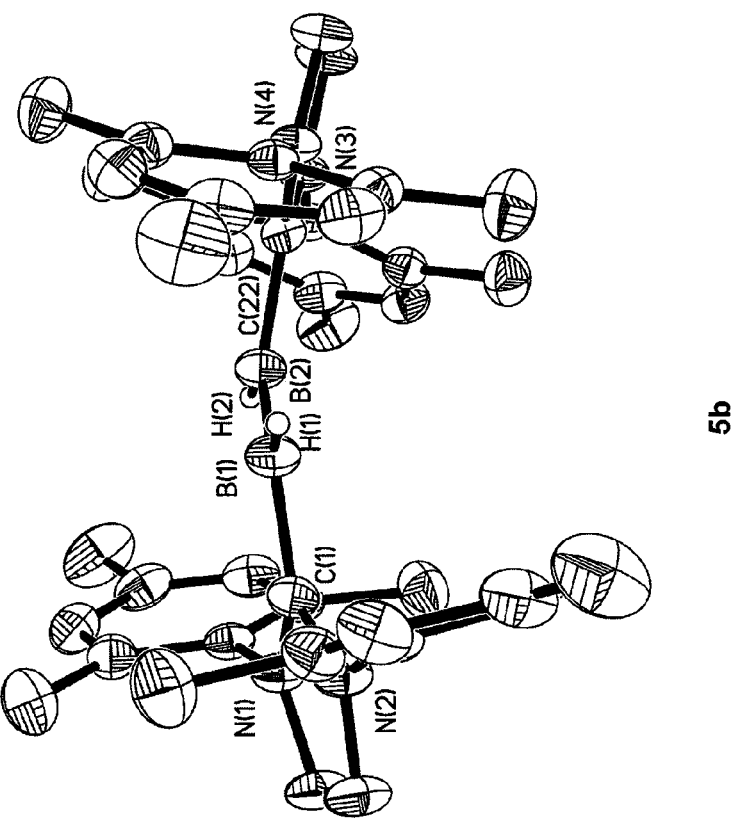

The trans-bent C(H)B=B(H)C boron-boron double bond is the most remarkable structural feature of 5c (FIG. 4). Its trans-bending angle, θ)=36°, is the same as that in the heavier Group 14 ethylene congener, [R(Mes)Ge=Ge(Mes)R] (R=2,6-Pr$^i$$_2$C$_6$H$_3$). The central B=B bond distance in 5c (1.679(9) Å) is 0.116 Å shorter than that of the corresponding B—B single bond of 4(1.795(5) Å), but it is about 0.1 Å longer than those in 3(1.560(18) Å, average), in dianionic (tetramino) diborates (1.566(9) to 1.59(1) Å), and in OC(H)B=B(H)CO (1.590 Å, computed). Notably, the B=B bond distance of 5c is only about 0.05 Å longer than in [Mes$_2$BB-(Mes)Ph]$^{2-}$-(1.636(11)Å) and [{Ph(Me$_2$N)BB(NMe$_2$)Ph}]$^{2-}$(1.627 Å, average). Each boron atom in 5c is pyramidal with a 344.3° bond angle sum. As far as we are aware, 5c is the first example of pyramidal tricoordinate boron in an acyclic environment. The cyclic silaborirane, CH$_2$SiH$_2$BH, and its analogs have been computed to have pyramidal geometries due to heteroatom-boron p orbital interactions. Constrained systems like 1-boraadamantane necessarily have nonplanar boron geometries.

In contrast to the trans-bent structure of 5c, isomer 5a possesses the same planar C(H)B=B(H)C core as observed in 3. Each boron atom in 5b (FIG. 4) also has a planar tricoordinate environment. However, 5b adopts a twisted geometry with a 18.1° dihedral angle between the two CBH planes. The B=B double bond distance of 5b (1.582(4) Å) is similar to those of 3(1.560(18) Å (average)) and 5a (1.602(5) Å). Remarkably, the B=B bond distance in the crystal structure of 5c (1.679(9) Å) is about 0.1 Å longer. The boron-boron double bond character of 5 is further supported by the $^π$B=B$^{-π*}$$_{B=B}$ absorption (λ$_{max}$) 574 nm).

The B3LYP/6-311+G** DFT optimization of 5, starting with the X-ray coordinates, led to a planar geometry and a B=B bond distance of 1.605 Å, essentially identical with the experimental value (1.602(5) Å) of planar 5a. The polymorphism exhibited by 5 may be attributed to the combination of a number of factors including (1) the flat potential energy surface; (2) the packing effects in crystals; (3) the polarity of the solvent used for crystallization; and (4) the intramolecular steric repulsion of the carbene ligands. The different packing patterns of 5a-c suggest that the associated distinct packing effects may contribute to the stabilization of these polymorphs. Differences in solvent polarity are known to significantly affect conformational isomerism of molecular and supramolecular systems. Indeed, 5a and 5b were isolated from 1:5 Et$_2$O/hexane solvent mixtures, whereas 5c was crystallized from pure Et$_2$O. Compared to the more sterically demanding ligands in 3, the smaller ligands in 5 can adjust their orientations more easily to packing forces.

Figure 5:
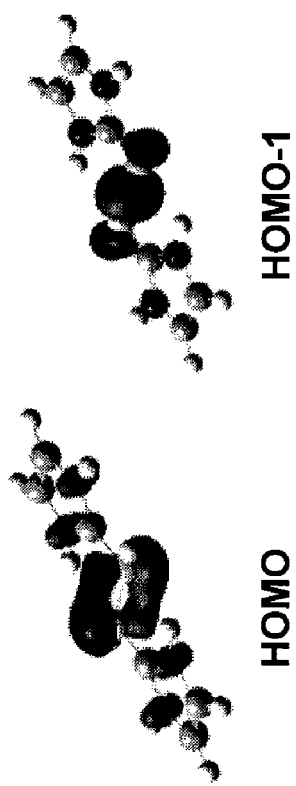
FIG. 5. Schematic representation of the frontier orbitals of trans-bent 5c.

Our numerous computations employing simplified ligand models R''(H)B=B(H)R'' (R''=C(NRCH)$_2$, with R=H or CH$_3$) confirmed the flatness of the potential energy surface. The planar 5a models had C$_{2h}$ symmetry. The C$_i$ models for trans-bent 5c optimized to the same C$_{2h}$ geometries. The only minimum (in C$_2$ symmetry) corresponding to 5b (R=CH$_3$) had a small planarization barrier. Consequently, the X-ray coordinates of 5c were used for the MO model shown in FIG. 5. Boron-boron π-bonding dominates the HOMO, while the HOMO-1 has mixed B—B and B—H σ bonding character (FIG. 5). The Wiberg (1.445) and NLMO/NPA (1.515) B—B bond indices, comparable to those reported for 3(1.408 and 1.656, respectively), support the presence of a B=B double bond in 5c despite its ca. 0.1 Å boron-boron elongation and trans-bent geometry. The distortion exhibited by 5c does not decrease the boron-boron bond order substantially and supports the dictum "the electronic structure, rather than bond distances, determines the nature of multiple bonds".

The experimental realization of three distinct polymorphic structures of diborene 5 may be attributed to a combination of, inter alia, packing effects in the crystal, crystallizing-solvent polarity, and intramolecular ligand steric effects.

Example 3

Synthesis and Characterization of R'(Cl)Si—Si(Cl)R' and R'Si=SiR'(R'=:C{N(2,6-Pr$^i$$_2$C$_6$H$_3$)CH}$_2$)

Figure 6:
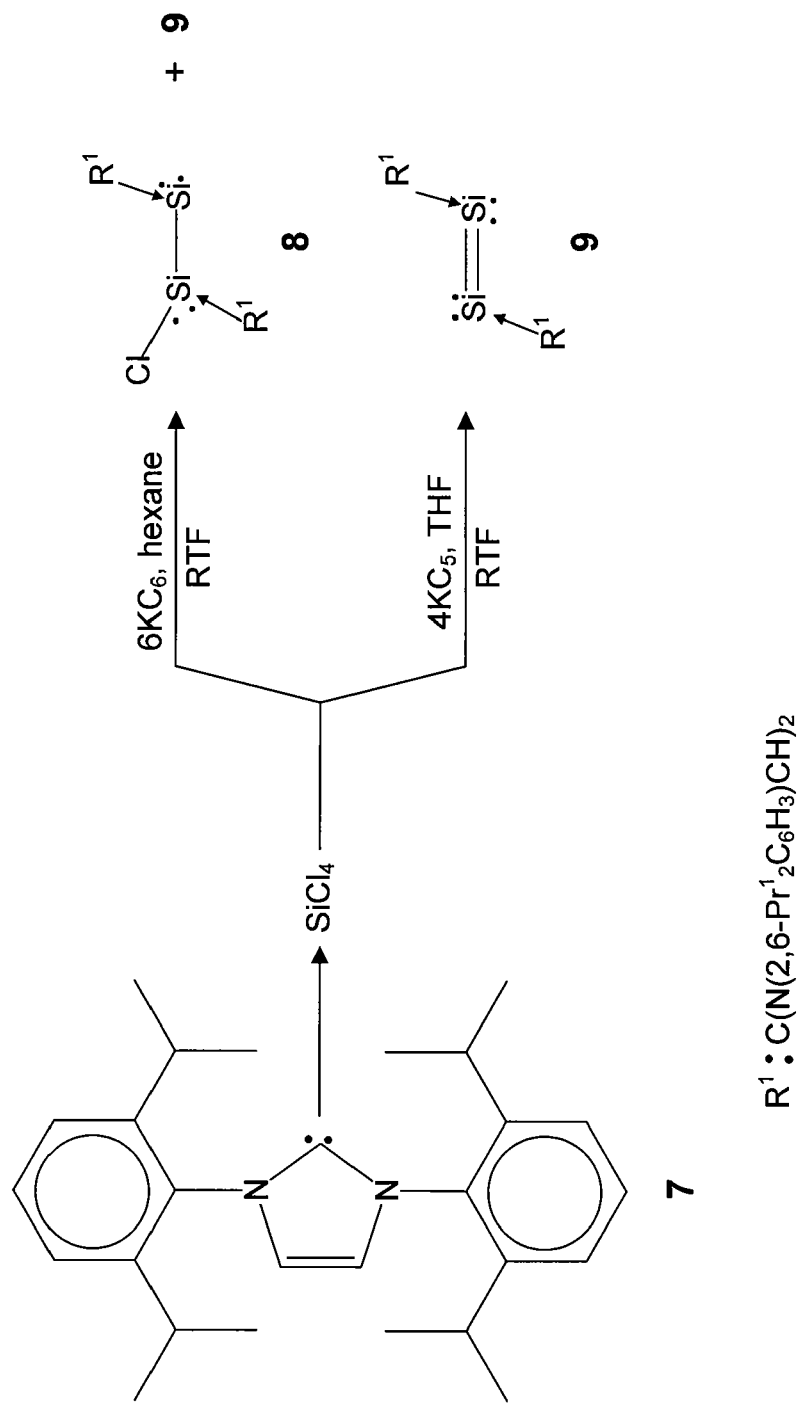
FIG. 6. Synthetic scheme for compounds R'(Cl)Si=Si(Cl)R' and R'Si=SiR', wherein R'=:C{N(2,6-Pr$^i_2$C$_6$H$_3$)CH}$_2$.

Kuhn et al. synthesized hypervalent L':SiCl$_4$ {where L': is :C[N(R)C(CH$_3$)]$_2$ and R is alkyl} complexes, which are neutral equivalents of [SiCl$_5$]$^-$. Consistently, we found that room-temperature reaction of a sterically demanding N-heterocyclic carbene ligand, R':, with SiCl$_4$ in hexane, gives R'SiCl$_4$, 7, in an essentially quantitative yield. The potassium graphite reduction of 7 (in a 1:KC$_8$ ratio of 1:6) in hexane produced air-sensitive, orange-red, sheetlike crystals of 8(6.1% yield) and air-sensitive, dark red, block crystals of 9 (as a minor product) (FIG. 6). However, when the potassium graphite reduction of 7 is performed (with a 1:KC$_8$ ratio of 1:4) in tetrahydrofuran (THF) (FIG. 1), compound 9 can be exclusively isolated and in higher yield (23.2%). In the $^1$H nuclear magnetic resonance (NMR) spectra, the imidazole resonances (in C$_6$D$_6$) of compounds 7, 8, and 9 appear at 6.40, 6.31, and 6.58 parts per million (ppm), respectively. The $^1$H-decoupled $^{29}$Si NMR spectra of compounds 7 to 9 were also determined. The $^{29}$Si NMR chemical shift of (in CD$_2$Cl$_2$), 108.9 ppm, is comparable to reported values (−104.7 to −105.9 ppm) of hypervalent Si compounds L':SiCl$_4$ {where L': is :C[N(R)C(CH$_3$)]$_2$ and R is alkyl}. The $^{29}$Si NMR resonance of 8 (in C$_6$D$_6$), 38.4 ppm, compares with 78.3 ppm of [C(H)N(tBu)]$_2$Si: and 14.6 ppm of [PhC(NtBu)$_2$]SiCl, but is at a considerably lower field than the −48.6 to −57.4 ppm range of silylene-isocyanide complexes. The $^{29}$Si chemical shift of 3 (in C$_6$D$_6$), 224.5 ppm, resides at an even lower field than typical disilene resonances (50 to 155 ppm).

The x-ray structural analysis of 8 (FIG. 7) reveals that the (Cl)Si—Si(Cl) core is sterically well-shielded by the two R' ligands. The central Si—Si bond distance, 2.393(3) Å, is only about 0.05 Å longer than the sum of Si covalent radii (2.34 Å) and about 0.03 Å longer than the Si—Si single-bond distance in α-silicon (2.36 Å). Each Si atom in 8, in the formal +1 oxidation state, is three-coordinate in a trigonal pyramidal geometry. The sum of the bond angles of the Si atoms in 7, 308.0° (mean), compares very well with that in (tBu$_2$MeSi)$_2$Si(F)Li.(THF)$_3$(307.6°) as well as with the computed value for Ph$_2$Si:CNPh (306.8°). The pyramidal geometry at each Si atom in 8 results from substantial lone electron-pair character on both Si atoms. The two R'(Cl)Si moieties of 8 adopt a gauche conformation [the Cl(1)-Si(1)-Si(2)-Cl(2) torsion angle is −46.5°]. These structural features of 8 are akin to those of its isolobal equivalent H$_2$P—PH$_2$, which also favors a gauche conformation. Although a Lewis base-stabilized silylene was reported a decade ago, 8 is noteworthy as a Lewis base stabilized his-silylene—namely, two silylene units bridged by a Si—Si bond. The Si—C bond distances [1.934 (6) Å, mean] of 8 are comparable to that of 1 [1.928(2) Å] (FIG. 6) whereas the mean Si—Cl bond distance [2.164(3) Å] of 8 matches the sum of the Si and Cl covalent radii (2.16 Å). The visible absorption maximum of 8($\lambda_{max}$=510 nm, in hexane) is similar to that of an intramolecularly base-stabilized three-coordinate silylene ($\lambda_{max}$=478 nm).

The nature of the bonding in 8 was delineated by density functional theory (DFT) computations at the B3LYP/6-311+G** level on the simplified L:(Cl)Si—Si(Cl):L [where L: is :C(NHCH)$_2$] model, 8-H. The computed Si—Si (2.405 Å) and Si—C (1.926 Å) bond distances of 8-H compare well with the experimental values [2.393(3) and 1.934(6) (mean) Å, respectively, of 8. The computed Si—Cl bond distance of 2.238 Å in 8-H is about 0.07 Å longer than that in 8-H [2.164(3) Å, mean]. The fact that the sum of the bond angles around the Si atoms in 8-H (298.2°) is smaller than that of 8(308.0°) may be attributed to the substantially lower steric crowding of the model ligands used in 8-H. The theoretical analysis of 8-H included both localized molecular orbitals (LMOs) and canonical molecular orbitals. The LMOs reveal a Si—Si σ bonding orbital and two nonbonding lone-pair orbitals, one at each Si atom. Natural bonding orbital (NBO) analysis shows that the Si—Si σ single bond [Wiberg bond index (WBI)=0.94] has 12.1% s-, 87.4% p-, and 0.5% d-character, whereas the nonbonding Si lone-pair orbitals have 68.3% s-. 31.6% p-, and 0.1% d-character. The Si—Cl bond has 8.5% s-, 89.9% p-, and 1.6% d-character.

We also examined the structure of the uncomplexed Si$_2$Cl$_2$ parent molecule. Unlike acetylenes and Sekiguchi's disilyne, a doubly-bridged (C$_{2v}$) Si(μ-Cl)$_2$Si geometry with a 102.1° dihedral angle between the two Si$_2$Cl rings is preferred in the 133 LYP/6-311+G* optimization, which compares with the doubly-bridged (C$_{2v}$) global minimum of Si$_2$H$_2$(26). The Si—Si bond distance, 2.361 Å, corresponds to a single Si—Si bond. The symmetrical Cl-bridged bonding elongates the Cl—Si distance (2.387 Å) and involves Cl lone pairs. However, in 8 these Cl-bridging interactions are replaced by the complexation of two-electron donor carbene ligands to the Si atoms.

Figure 7:
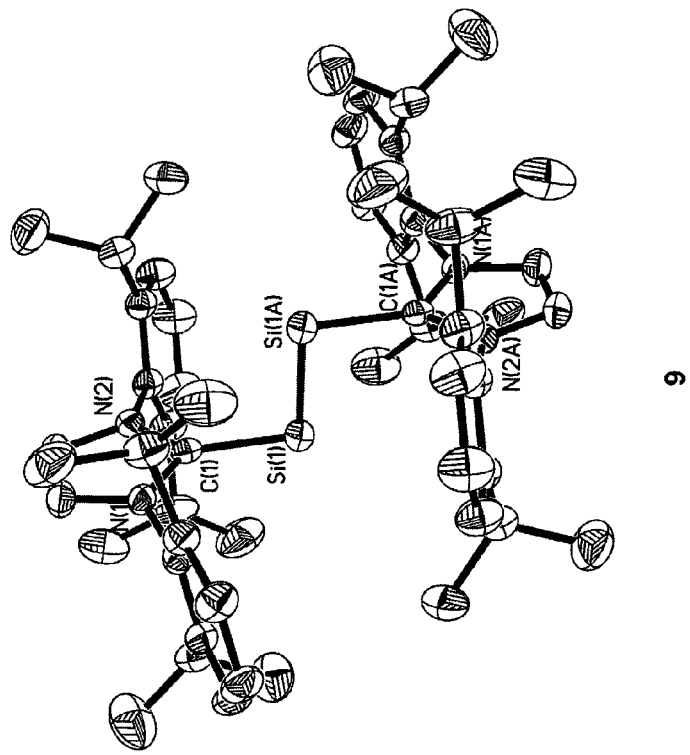
FIG. 7. Molecular structures of R'(Cl)Si=Si(Cl)R' 8 and R'Si=SiR' 9, wherein R'=:C{N(2,6-Pr$^i_2$C$_6$H$_3$)CH}$_2$. Thermal ellipsoids represent 30% probability. Hydrogen atoms were omitted for clarity. Selected bond distances (Å) and angles (deg) for 8 are Si(1)-Si(2), 2.393(3); Si(1)-C(1), 1.939(6); Si(1)-Cl(1), 2.161(3); Si(2)-C(28), 1.929(7); Si(2)-Cl(2), 2.168(3); C(1)-Si(1)-Si(2), 98.76(19); Cl(1)-Si(1)-Si(2), 108.75(11); C(1)-Si(1)-Cl(1), 101.2(2); C(28)-Si(2)-Si(1), 98.7(2); Cl(2)-Si(2)-Si(1), 107.96(11); and C(28)-Si(2)-Cl(2), 100.7(2). Selected bond distances (Å) and angles (deg) for 9 are Si(1A)-Si(2), 2.2294(11); Si(1)-C(1), 1.9271(15); and C(1)-Si(1)-Si(1A), 93.37(5).
Figure 7:
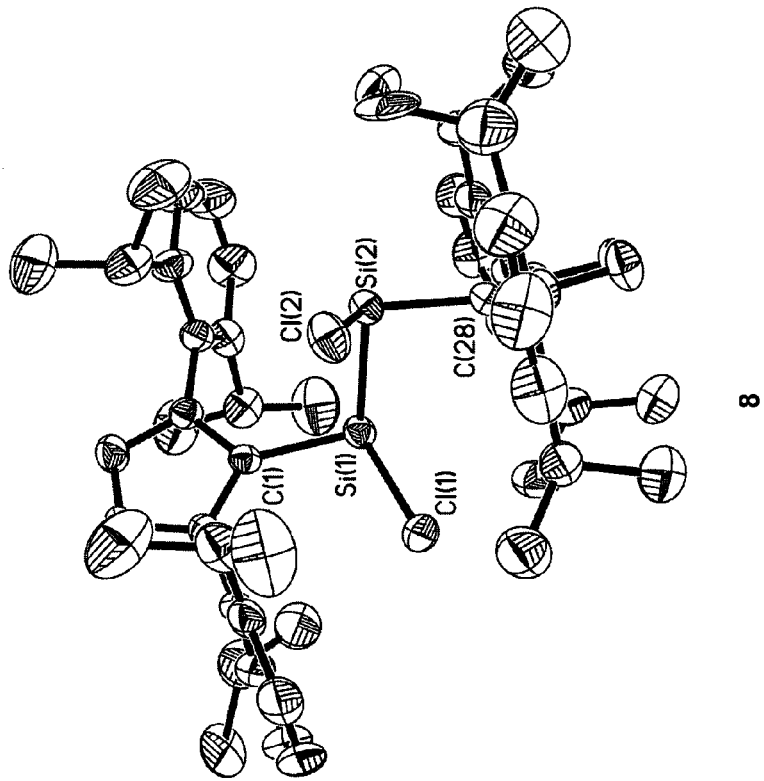

One structural feature of 9, of C$_i$ symmetry, is the core (FIG. 7). The Si=Si bond distance in 9, 2.2294(11) Å, is within the reported range of disilene bond distances (2.14 to 2.29 Å) and compares well with the computed [2.249 Å, BI-ILYP; 2.281 Å, B3LYP] and experimental (2.246 Å) bond distances of Si$_2$. Both OC:Si=Si:CO (2.310 Å, B3LYP) and singlet Si$_2$H$_2{}^{2-}$ (2.288 Å, B3LYP) suggest further comparisons. The Si—Si double-bond character of 9 is further supported by the $\pi_{Si=Si}$–$\pi^*_{Si=Si}$ absorption ($\lambda_{max}$=466 nm, in THF), which is comparable to the reported ultraviolet visible absorption maxima (390 to 480 nm) of stable disilenes. However, in contrast to previously reported disilenes, in which three-coordinate Si atoms (in the +2 formal oxidation state) reside in trigonal planar environments, the Si atoms in 9—in the formal oxidation state of zero—are only two-coordinate and have transbent geometries with C—Si=Si angles of 93.37(5)°. The two parallel carbene ligands are bound almost perpendicularly to the central Si=Si double bond. Generally, Si does not hybridize extensively. The almost-90° transbent skeletal conformation is consistent with the predominantly 3p-character of the Si—Si bonding orbitals in 9 and the predominantly 3s-character of the Si lone-pair molecular orbitals (see the NBO analysis below). Indeed, the nearly orthogonal transbent conformation of 9 is shared by the OC:Si—Si:CO complex, the dianionic Si$_2$H$_2{}^{2-}$, and the simple valence isoelectronic HP=PH model of the diatomic molecules of the Group 15 element (dipnictenes) family, RË=ËR (E=P, As, Sb, Bi), all of which possess an electron lone pair on the central core (E) atoms. The Si—C bonds [1.9271(15) Å] of 9 are only marginally shorter than those of 1 and 2. The fact that no $^{29}$Si—$^1$H coupling was observed in the $^1$H-coupled $^{29}$Si NMR spectrum further supports the formulation of 9.

Figure 8:
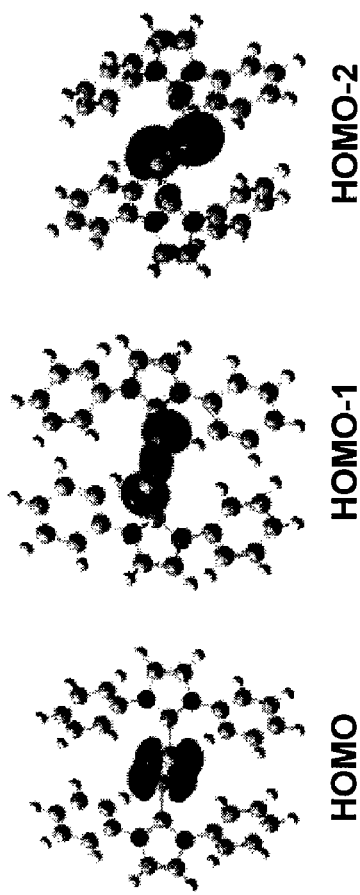
FIG. 8. The HOMO (π), HOMO-1 (σ), and HOMO-2(lone pair) of 8-Ph.

Density Functional Theory (DFT) computations at the B3LYP/6-311+G** level on the simplified L:Si=Si:L; {where L: is :C[N(C$_6$H$_5$)CH]$_2$} model, 9-Ph. support the bonding analysis. The computed Si=Si bond distance (2.2407 Å), the Si—Si—C bond angle (99.2°), and the C—Si—Si—C torsion angle (180.0°) are very close to the experimental values of 9 [d$_{Si=Si}$=2.2294(11) Å; Si—Si—C bond angle=93.37(5)°, C—Si—Si—C torsion angle=180.0°]. The highest occupied molecular orbital (HOMO) corresponds to the Si—Si π bond, whereas the HOMO-1 is dominated by the Si—Si σ bond. The HOMO-2 is one of the two nonbonding lone-pair molecular orbitals (FIG. 8).

The molecular orbital (MO) profile of 9-Ph differs from that of the triplet (X$^3\Sigma_g^-$) ground state of the isolated Si$_2$ species, in which each of the two degenerate 1π$_u$ MOs are occupied by one electron with the same spin. Complexation of Si$_2$ by two carbene ligands (as electron-pair donors) results in the occupancy of all valence orbitals of Si. Indeed, the Wiberg bond index (WBI), 1.73, is supportive of a Si=Si double bond in 9-Ph. NBO analysis characterizes the occupancies of the Si—Si σ bond as 17.3% s, 82.2% p, and 0.5% d, the Si—Si π bond as 0.0% s, 99.6% p, and 0.4% d, and the Si lone-pair nonbonding orbitals as 72.8% s, 27.2% p, and 0.0% d.

The B3LYP/6-311+G** computed binding energies [zero point energy-corrected] of the carbene ligand models {where L: is :C[N(Me)CH]$_2$}; to the Si-based cores are particularly noteworthy (Eqs. 1 to 3)

$$SiCl_4 + L: \rightarrow L:SiCl_4(7\text{-Me}) - 10.6 \text{ kcal/mol} \quad (1)$$

$$Si_2Cl_2(C_{2v}) + 2L: \rightarrow L:(Cl)Si\text{---}Si(Cl):L(8\text{-Me}) - 69.4 \text{ kcal/mol} \quad (2)$$

$$Si_2(X^3\Sigma_g^-) + 2L: \rightarrow L:Si\text{=}Si:L(9\text{-Me}) - 80.9 \text{ kcal/mol} \quad (3)$$

The very large binding energies of 8-Me and 9-Me reflect the coordinatively unsaturated character of $Si_2(X^3\Sigma_g^-)$ and of $Si_2Cl_2(C_{2v})$, respectively, as well as the remarkable complexation proclivity of the carbene ligand. Bulky N-heterocyclic carbene ligands are further demonstrated to be effective lone-pair donors capable of stabilizing—both thermodynamically and kinetically—unusual molecules.

Example 4

Synthesis and Characterization of R'P—PR' (R'= :C{N(2,6-Pr$^i_2$C$_6$H$_3$)CH}$_2$ or :C{N(2,4,6-Me$_3$C$_6$H$_2$)CH}$_2$)

While the free P$_2$ molecule, :P≡P:, possesses a phosphorus-phosphorus triple bond, compounds 10 and 11 exhibit a unique bisphosphinidene structure: two phosphinidene units, each with two lone pairs of electrons, bridged by a phosphorus-phosphorus single bond.

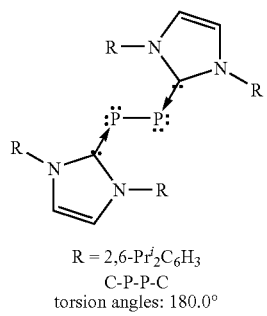

R = 2,6-Pr$^i_2$C$_6$H$_3$
C-P-P-C
torsion angles: 180.0°

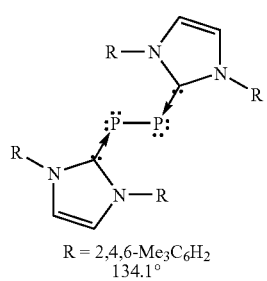

R = 2,4,6-Me$_3$C$_6$H$_2$
134.1°

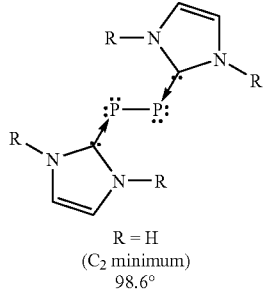

R = H
(C$_2$ minimum)
98.6°

Figure 9:
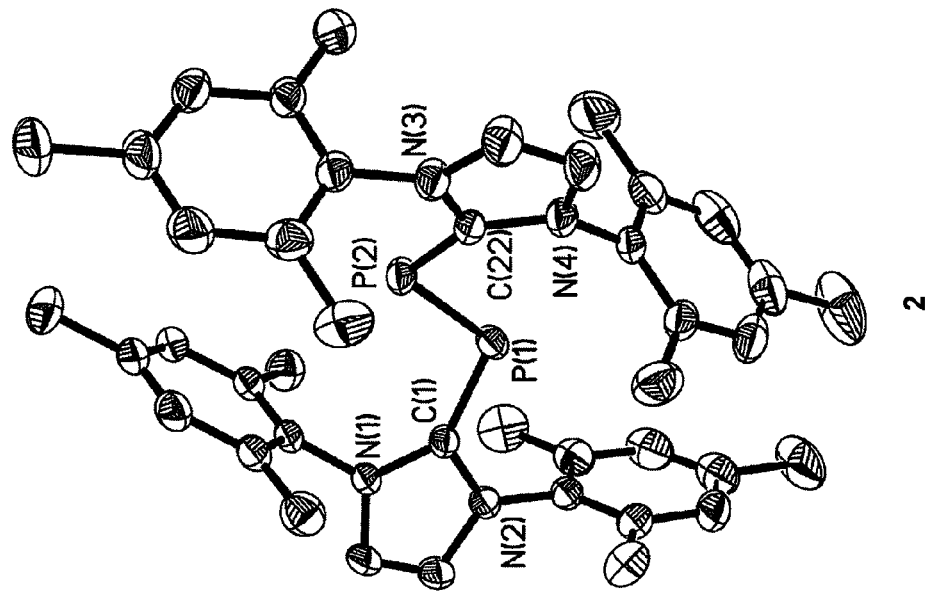
FIG. 9. Molecular structures of 10 and 11 (thermal ellipsoid represents 30% probability; hydrogen atoms omitted for clarity). Selected bond distances (Å) and angles (deg) for 10 P(1)-P(1A), 2.2052(10); P(1)-C(1), 1.7504(17); C(1)-P(1)-P(1A), 103.19(6). Selected bond distances (Å) and angles (deg) for 11 are P(1)-P(12), 2.1897(11); P(1)-C(1), 1.754(3); P(2)-C(22), 1.754(3); C(1)-P(1)-P(2), 102.57(10); C(22)-P(2)-P(1), 103.01(10).
Figure 9:
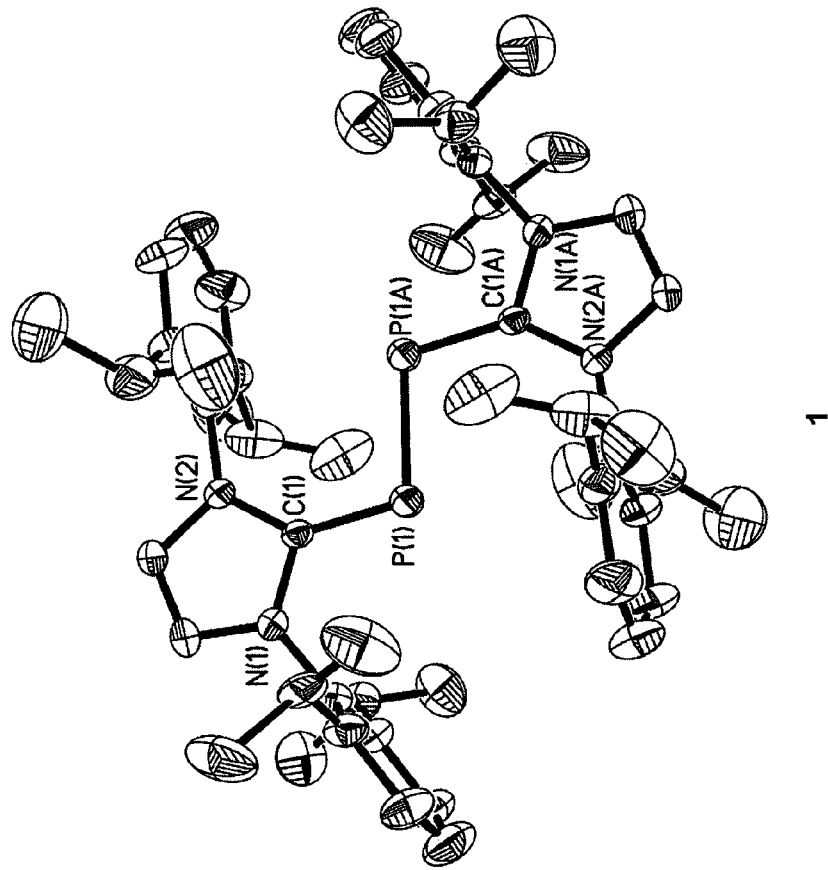

We prepared R'PCl$_3$ by combining R' ligands with PCl$_3$. The potassium graphite reduction of R'PCl$_3$(R'PCl$_3$/KC$_8$ ratio of 1:3.1) in THF affords the carbenestabilized diphosphorus R'P—PR' compounds, 10 (R'=:C{N(2,6-Pr$^i_2$C$_6$H$_3$)CH}$_2$) and 11 (R'=:C{N(2,4,6-Me$_3$C$_6$H$_2$)CH}$_2$), respectively (FIG. 9). Both 10 and 11 were isolated as moisture- and air-sensitive red crystals in moderate yields (10, 56.6%; 11, 20.7%). The $^1$H NMR imidazole resonances (C—H) of 10 and 11 are 5.98 and 5.71 ppm, respectively. The $^1$H-coupled $^{31}$P NMR singlet resonances, −52.4 and −73.6 ppm for 10 and 11, respectively, are comparable to those of other carbene-phosphinidene adducts L:P(Ph), −53.5 ppm (L:=tetramethylimidazol-2-ylidene) (12a) and −23.0 ppm (L:=:C{N(2,4,6-Me$_3$C$_6$H$_2$)CH}$_2$) (12b), but are quite different from those (34 to 54 ppm) of diphosphabutadienes, (R$_2$N)$_2$C=P—P=C(NR$_2$)$_2$ (R=Me, Et). The lack of detectable $^{31}$P-$^1$H coupling in 10 and 11 also supports the assigned structures.

Compound 10 has C$_i$ symmetry and a trans-bent geometry with a 180.0° C.(1)-P(1)-P(1A)-C(1A) torsion angle about the central P—P bond. The P—P bond distance, 2.205 Å, compares well to the 2.21 Å P—P single bond distance in T$_d$ P$_4$. The C(1)-P(1)-P(1A) bond angle (103.2°) corresponds to the 110° C—P—P angle (average) in the R'[P—P=P—P]: carbene adduct, 13, and the computed C—P—P angles in both H$_2$C=P—P=CH$_2$(14, C$_{2h}$) (101.2°) and H$_3$CP=PCH$_3$ (15, C$_{2h}$) (99.9°). Hence, the C—P—P angle does not help delineate the nature of the P—C$_{NHC}$ bonding. Notably, the two imidazole rings and the P—P bond of 10 are almost coplanar (the N($_2$)-C(1)-P(1)-P(1A) torsion angle is 2.3°; this value is 8.2° (average) in 11). The P—C bond length (1.750 Å) in 10, similar to those (1.75-1.79 Å) in 11-13, is between the 1.65-1.67 Å P=C double bond lengths of the nonconjugated phosphaalkenes and the normal P—C single bond distance (i.e., the 1.839 Å P—C lengths in 12b and the computed 1.87 Å in 15). Two interpretations of the bonding in 10, 10A (bis-phosphinidene), and 10B (bis-phosphaalkene) (Eq. 4) are akin to two resonance forms of carbene-phosphinidene adducts. Donation of the two carbene electron lone pairs to P decreases the phosphorus-phosphorus bond order from three in :P=P: to one in 10A or 10B.

The P=C double bond character implied by 10B inhibits, however, the imidazole π-delocalization and should be consistent with the $^{31}$P NMR chemical shifts (34 to 54 ppm) of the diphosphabutadienes. Instead, the high-field $^{31}$P NMR chemical shift (−52.4 ppm) of 10 favors 10A as the predominate formulation.

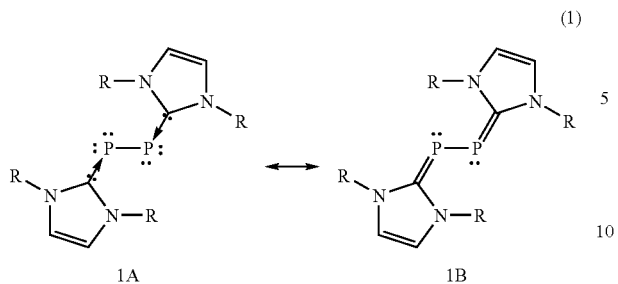

1A            1B

Our DFT computations on the simplified L:P—P:L model, 10-H, support this interpretation. Optimization of 10-H($C_{2h}$ symmetry) affords the same trans-bent conformation as that for 10, but with one imaginary frequency corresponding to a rotational transition state. Notably, the ca. 7 kcal/mol more stable gauche minimum of 10-H($C_2$ symmetry) (C—P—P—C torsion angle=98.6°) resembles that of the isolobal $H_2S_2$(H—S—S—H torsion angle=90.6°). The sensitivity of the conformation about the P—P bond to the steric effects of the nearby carbene ligands (shown clearly by inspecting space-filling models) was confirmed by preparing 11, which has a smaller carbene ligand than 10. Although having bond distances similar to those for 10, compound 11 adopts a gauche conformation. The C(1)-P(1)-P(2)-C(22) torsion angle (134.1°) of 11 lies between the 180° of 10 and the 98.6° of 10-H ($C_2$ minimum).

Figure 10:
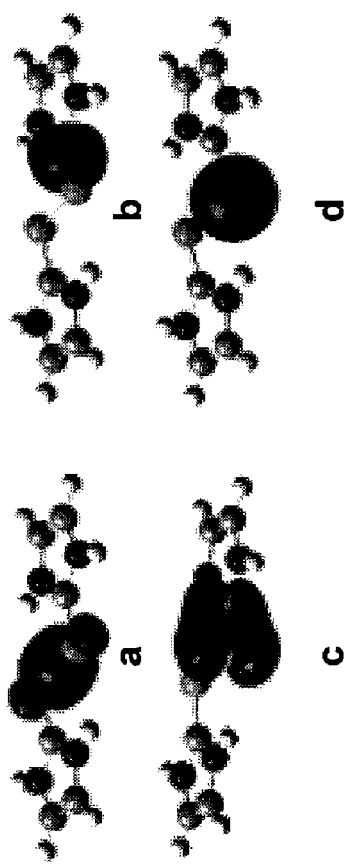
FIG. 10. Localized molecular orbital (LMOs) of 10-H with C$_{2h}$ symmetry. (a) P—P σ-bonding orbital; (b) P—C σ-bonding orbital; (c) lone pair orbital (mainly p-character) with pπ back-donation to the empty p orbital of C$_{NHC}$; (d) lone pair orbital (mainly s-character).

The LMOs of the simplified models (with L:=:C(NHCH)$_2$) 10-H (optimized in both $C_{2h}$ (FIG. 10) and $C_2$ symmetries) and 11-H (employing the X-ray coordinates of 11) are quite similar. All LMOs have one P—P σ-bond (FIG. 10a), one P—C σ-bond (FIG. 10b), and two lone-pair orbitals on each P atom (FIGS. 10c and 10d). As exemplified in the 10-H model ($C_{2h}$), (d) has mainly s-character (68.8% s, 31.2% p, 0.0% d) according to NBO analysis, while (c) is essentially pure p (0.0% s, 99.8% p, 0.2% d), but involving modest interaction with the p orbital of $C_{NHC}$ as implied by 10B. This pπ back-donation, involving 64.8% P and 35.2% C components, results in modest P=C double bond character and is consistent with the structural data of 10 (i.e., the coplanarity of the imidazole rings and the P$_2$ unit, the 1.750 Å P—C bond distance, and the 1.397 P—C WBI). The P—C σ bond polarization is 64.8% toward carbon and 35.2% toward phosphorus that has 20.7% s-, 78.6% p-, and 0.7% d-character. The P—P bond is single (WBI=1.004) with 11.5% s-, 87.9% p-, and 0.6% d-character. Thus, like the silicon atoms in R'Si=SiR' and third-period elements generally, the phosphorus atoms in 10 and 11 do not hybridize extensively. Notably, the P$_2$ unit in the R'P—PR' molecules is demonstrated to serve as electron pair acceptors, thereby mimicking the behavior of a Lewis acid.

All examples included in this application are for the purpose of illustration of the invention only and are not intended in any way to limit the scope of the present invention. It will thus be readily apparent to one skilled in the art that varying substitutions and modifications may be made to the invention disclosed herein without departing from the scope and spirit of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention.

All documents cited within this entire application, including journal articles or abstracts, published or corresponding U.S. or foreign patent applications, issued or foreign patents, or any other documents, are each entirely incorporated by reference herein, including all data, tables, figures, and text presented in the cited documents.

We claim:

1. A stable neutral compound of formula:

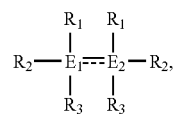

wherein:

$R_1$ is a persistent carbene selected from the group consisting of imidazole-2-ylidenes, triazole-5-ylidenes, cyclic diaminocarbenes, acyclic diaminocarbenes, heteroaminocarbenes, and combinations thereof;

$R_2$ and $R_3$ are, independently of each other, absent or are selected from the group consisting of: H, F, Br, Cl, I, and combinations thereof;

and E is B, Si, or P;

with the proviso that:

when E is B, ------is ==, $R_2$ is absent and $R_3$ is H, F, Br, or Cl;

when E is B and ------is =, $R_2$ and $R_3$ are, independently of each other, H, F, Br, or Cl;

when E is Si, and ------is ==, both $R_2$ and $R_3$ are absent;

when E is Si, and ------is —, $R_2$ is absent and $R_3$ is H, F, Br, Cl, or I;

when E is P and ------is —, both $R_2$ and $R_3$ are absent.

2. The compound of claim 1, wherein $R_1$ is the carbene selected from the group consisting of :C{N(SiR$^x_3$)CH}$_2$, wherein R$^x$ is methyl, tert-butyl, monoalkylaryl, dialkylaryl, trialkylaryl, dialkylamido, :C{N(2,6-Pr$^i_2$C$_6$R$^y_3$)CH}$_2$, :C(NHCH)$_2$, :C{N(Pr$^i$)C(CR$^y_3$)}$_2$, :C{N(2,4,6-Me$_3$C$_6$R$^y_2$)CH}$_2$, wherein R$^y$ is, independently, H, F, Br, Cl, or I, and combinations thereof.

3. The compound of claim 2, represented by the formula:

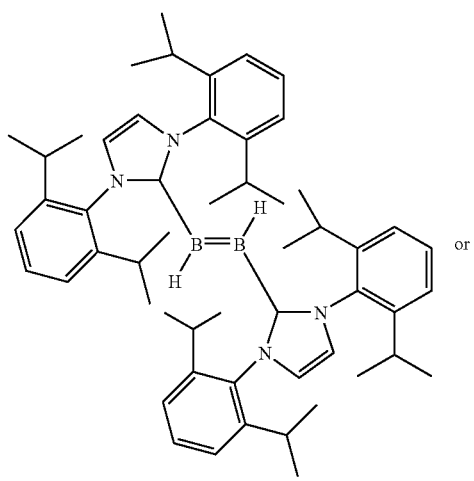

or

23
-continued
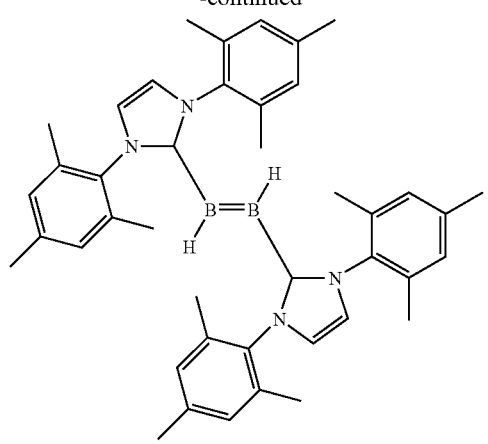
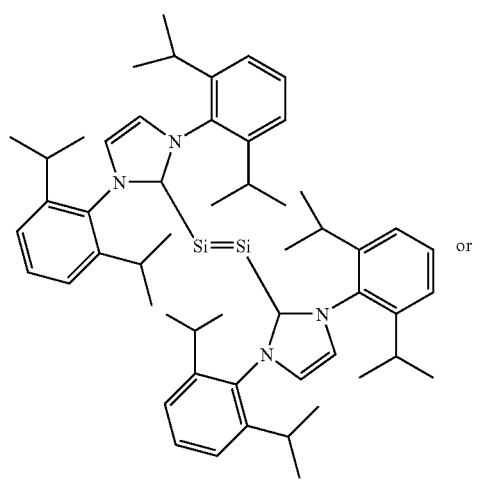
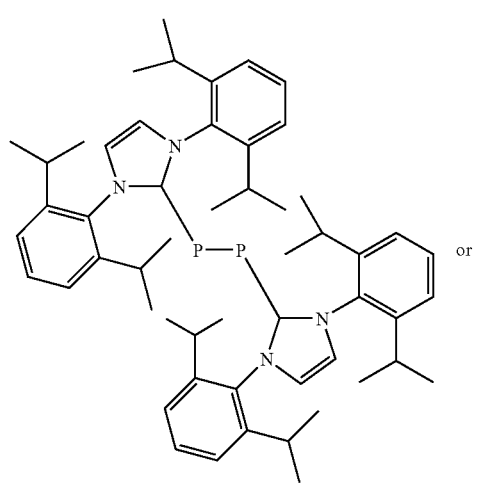
24
-continued
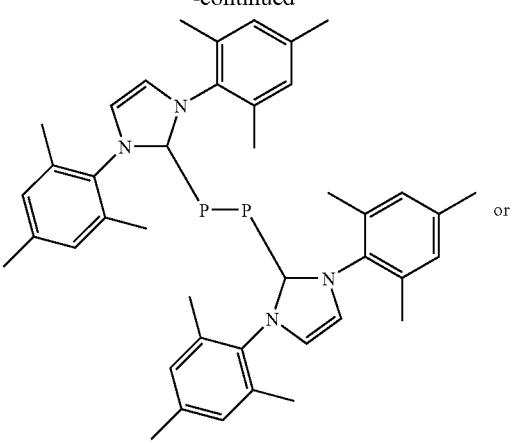 or
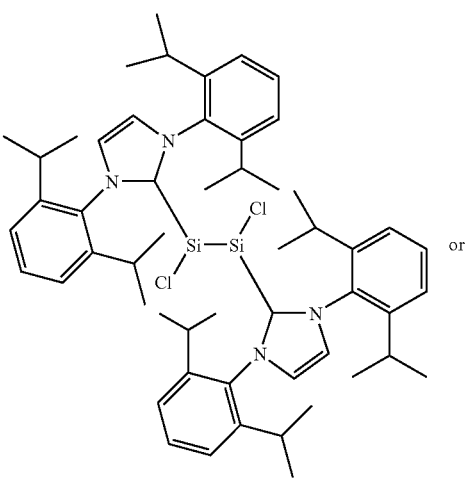 or
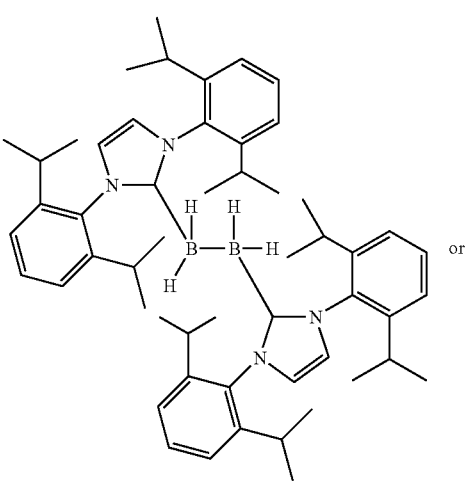 or

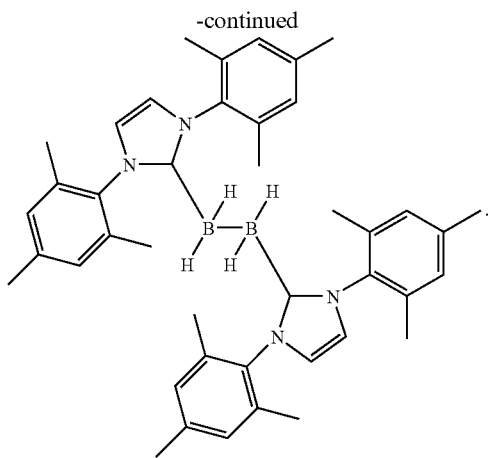

4. A method of making a stable neutral compound of a formula:

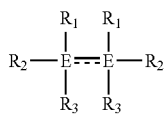

wherein:

$R_1$ is a persistent carbene selected from the group consisting of imidazole-2-ylidenes, triazole-5-ylidenes, cyclic diaminocarbenes, acyclic diaminocarbenes, heteroaminocarbenes, and combinations thereof;

$R_2$ and $R_3$ are, independently of each other, absent or are selected from the group consisting of: H, F, Br, Cl, I, and combinations thereof;

and E is B, Si, or P;

with the proviso that:

when E is B, and ===== is =, $R_2$ is absent and $R_3$ is H, F, Br, or Cl;

when E is B and ===== is =, $R_2$ and $R_3$ are, independently of each other, H, F, Br, or Cl;

when E is Si, and ===== is =, both $R_2$ and $R_3$ are absent;

when E is Si, and ===== is —, $R_2$ is absent and $R_3$ H, F, Br, Cl, or I;

when E is P and ===== is —, both $R_2$ and $R_3$ are absent;

said method comprising:

(a) reacting a compound of the formula

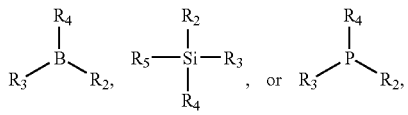

wherein $R_4$ and $R_5$ are, independently of each other, selected from the group consisting of: H, F, Br, Cl, and I, with $R_1$, thus forming:

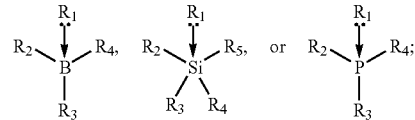

(b) reacting a product formed in (a) with a reducing agent in a solvent selected from the group consisting of dimethyl ether, diethyl ether, THF, dioxane, dimethoxyethane, methoxybenzene, and ethylene oxide, and combinations thereof; and (c) isolating

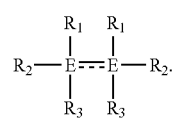

5. The method of claim 4, wherein the reducing agent is selected from the group consisting of $KC_8$, $LiAlH_4$, $NaBH_4$, DIBAL, Na(Hg), Na—K alloy, K(Hg), LiH, alkali and alkali earth metals, nascent hydrogen, and combinations thereof.

6. The method of claim 5, wherein the reducing agent is $KC_8$.

7. The method of claim 4, wherein the ratio of

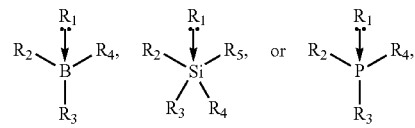

wherein $R_2$, $R_3$, $R_4$, and $R_5$ are, independently of each other, selected from the group consisting of: H, F, Br, Cl, and I, to the reducing agent is about 1 to about 10.

8. The method of claim 4, wherein the ratio of

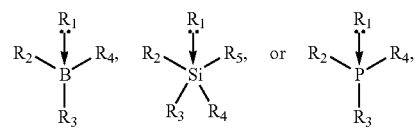

wherein $R_2$, $R_3$, $R_4$, and $R_5$ are, independently of each other, selected from the group consisting of: H, F, Br, Cl, and I, to the reducing agent is about 1 to about 6.

9. The method of claim 4, wherein the ratio of

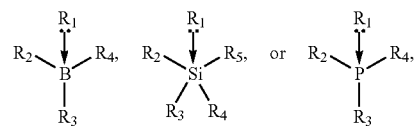

wherein $R_2$, $R_3$, $R_4$, and $R_5$ are, independently of each other, selected from the group consisting of: H, F, Br, Cl, and I, to the reducing agent is about 1 to about 5.

10. The method of claim 4, wherein the ratio of

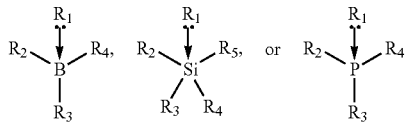

wherein $R_2$, $R_3$, $R_4$, and $R_5$ are, independently of each other, selected from the group consisting of: H, F, Br, Cl, and I, to the reducing agent is about 1 to about 4.

11. The method of claim 10, wherein the ratio between $R_1SiCl_4$, wherein $R_1$ is :C{N(2,6-Pr$^i_2$C$_6$H$_3$)CH}$_2$, and KC$_8$ is 1:4.

12. The method of claim 9, wherein the ratio between $R_1BBr_3$, wherein $R_1$ is :C{N(2,6-Pr$^i_2$C$_6$H$_3$)CH}$_2$, and KC$_8$ is 1:5.4.

13. The method of claim 9, wherein the ratio between $R_1BBr_3$, wherein $R_1$ is :C{N(2,4,6-Me$_3$C$_6$H$_2$)CH}$_2$, and KC$_8$ is 1:5.

* * * * *